(12) United States Patent
Quintero et al.

(10) Patent No.: US 11,980,354 B2
(45) Date of Patent: May 14, 2024

(54) SCAFFOLDS FOR JOINING LAYERS OF TISSUE AT DISCRETE POINTS

(71) Applicant: Ethicon, Inc., Somerville, NJ (US)

(72) Inventors: Julian Quintero, Flemington, NJ (US); Leo B. Kriksunov, Ithaca, NY (US); Robert J. Tannhauser, Bridgewater, NJ (US)

(73) Assignee: Ethicon, Inc., Raritan, NJ (US)

( * ) Notice: Subject to any disclaimer, the term of this patent is extended or adjusted under 35 U.S.C. 154(b) by 561 days.

(21) Appl. No.: 17/021,601

(22) Filed: Sep. 15, 2020

(65) Prior Publication Data

US 2020/0405278 A1     Dec. 31, 2020

Related U.S. Application Data

(62) Division of application No. 15/467,239, filed on Mar. 23, 2017.

(51) Int. Cl.
*A61B 17/00* (2006.01)
*A61F 2/00* (2006.01)
(Continued)

(52) U.S. Cl.
CPC .... *A61B 17/0057* (2013.01); *A61B 17/00491* (2013.01); *A61F 5/0083* (2013.01); *A61L 27/34* (2013.01); *A61L 27/58* (2013.01); *A61B 2017/00504* (2013.01); *A61B 2017/0065* (2013.01); *A61B 2017/00659* (2013.01); *A61B 2017/1139* (2013.01); *A61F 2/0063* (2013.01)

(58) Field of Classification Search
CPC ..... A61B 17/08; A61B 17/085; A61F 2/0063; A61F 5/0083; A61F 13/025; A61F 2002/0068; A61F 2002/0072
See application file for complete search history.

(56) References Cited

U.S. PATENT DOCUMENTS

| 167,162 A | 8/1875 | French |
| 2,508,855 A | 5/1950 | Brown |

(Continued)

FOREIGN PATENT DOCUMENTS

| CA | 2262408 A1 | 8/2000 |
| CN | 1352540 A | 6/2002 |

(Continued)

OTHER PUBLICATIONS

Tissuglu, TissuGlu FDA Summary of Safety and Effectiveness Data, Cohera Medical, Inc, Feb. 3, 2014, pp. 1-40, page number.

(Continued)

*Primary Examiner* — Sarah A Long
*Assistant Examiner* — Lindsey Bachman

(57) ABSTRACT

A device for joining two layers of tissue, comprises a substantially flat and flexible scaffold having an upper surface, a lower surface and sidewalls; a plurality of first passages penetrating said scaffold from said upper surface to said lower surface; a plurality of second passages penetrating said scaffold from said upper surface to said lower surface; a substantially flat and flexible top cover releasably attached to said upper surface and covering all of said upper surface; said top cover having a plurality of top cover passages aligned with said first plurality of passages.

10 Claims, 16 Drawing Sheets

(51) Int. Cl.
  *A61F 5/00* (2006.01)
  *A61L 27/34* (2006.01)
  *A61L 27/58* (2006.01)
  *A61B 17/11* (2006.01)

(56) References Cited

U.S. PATENT DOCUMENTS

| | | |
|---|---|---|
| 2,721,858 A | 10/1955 | Joyner |
| 2,722,220 A | 11/1955 | Mestrand |
| 2,807,262 A | 9/1957 | Lew |
| 2,905,174 A | 9/1959 | Smith |
| 3,254,111 A | 5/1966 | Hawkins |
| 3,402,716 A | 9/1968 | Baxter |
| 3,520,300 A | 7/1970 | Flower, Jr. |
| 3,731,683 A | 5/1973 | Zaffaroni |
| 3,888,247 A | 6/1975 | Stenvall |
| 3,940,362 A | 2/1976 | Overhults |
| 3,983,878 A | 10/1976 | Kawchitch |
| 3,995,641 A | 12/1976 | Kronenthal |
| 4,068,664 A | 1/1978 | Sharp |
| 4,080,348 A | 3/1978 | Korpman |
| 4,126,130 A | 11/1978 | Cowden et al. |
| 4,140,115 A | 2/1979 | Schonfeld |
| 4,263,906 A | 4/1981 | Finley |
| 4,313,865 A | 2/1982 | Teramoto |
| 4,340,043 A | 7/1982 | Seymour |
| 4,364,876 A | 12/1982 | Kimura |
| 4,390,519 A | 6/1983 | Sawyer |
| 4,460,369 A | 7/1984 | Seymour |
| 4,560,723 A | 12/1985 | Millet |
| 4,584,355 A | 4/1986 | Blizzard |
| 4,585,836 A | 4/1986 | Homan |
| 4,591,622 A | 5/1986 | Blizzard |
| 4,612,230 A | 9/1986 | Liland |
| 4,614,183 A | 9/1986 | Mccracken |
| 4,630,603 A | 12/1986 | Greenway |
| 4,655,767 A | 4/1987 | Woodard |
| 4,671,266 A | 6/1987 | Lengyel |
| 4,720,513 A | 1/1988 | Kameyama |
| 4,733,659 A | 3/1988 | Edenbaum |
| 4,767,401 A | 8/1988 | Seiderman |
| 4,793,887 A | 12/1988 | Card |
| 4,793,888 A | 12/1988 | Card |
| 4,795,435 A | 1/1989 | Steer |
| 4,852,571 A | 8/1989 | Gadsby et al. |
| 4,867,747 A | 9/1989 | Yarger |
| 4,872,450 A | 10/1989 | Austad |
| 4,950,282 A | 8/1990 | Beisang |
| 4,966,605 A | 10/1990 | Thieler |
| 4,999,235 A | 3/1991 | Lunn |
| 5,035,687 A | 7/1991 | Sandbank |
| 5,059,424 A | 10/1991 | Cartmell |
| 5,086,763 A | 2/1992 | Hathman |
| 5,088,483 A | 2/1992 | Heinecke |
| 5,106,362 A | 4/1992 | Gilman |
| 5,125,907 A | 6/1992 | Philpott |
| 5,164,444 A | 11/1992 | Bernard |
| 5,173,302 A | 12/1992 | Holmblad |
| 5,232,958 A | 8/1993 | Mallya |
| 5,254,132 A | 10/1993 | Barley |
| 5,259,835 A * | 11/1993 | Clark ............... A61F 13/0246 604/289 |
| 5,266,371 A | 11/1993 | Sugii |
| 5,308,313 A | 5/1994 | Karami |
| 5,328,687 A | 7/1994 | Leung |
| 5,336,209 A | 8/1994 | Porzilli |
| 5,415,626 A | 5/1995 | Goodman |
| 5,429,592 A | 7/1995 | Jensen |
| 5,445,597 A | 8/1995 | Clark |
| 5,449,340 A | 9/1995 | Tollini |
| D363,126 S | 10/1995 | Dusek |
| 5,456,660 A | 10/1995 | Reich |
| 5,476,440 A | 12/1995 | Edenbaum |
| 5,486,547 A | 1/1996 | Matsuda |
| 5,571,079 A | 11/1996 | Bello |
| 5,575,997 A | 11/1996 | Leung |
| 5,582,834 A | 12/1996 | Leung |
| 5,599,858 A | 2/1997 | Buchanan |
| 5,620,702 A | 4/1997 | Podell |
| 5,623,011 A | 4/1997 | Bernard |
| 5,624,669 A | 4/1997 | Leung |
| D382,343 S | 8/1997 | Wandell et al. |
| 5,653,769 A | 8/1997 | Barley, Jr. |
| D383,211 S | 9/1997 | Dunshee et al. |
| 5,662,599 A | 9/1997 | Reich |
| D387,169 S | 12/1997 | Dunshee et al. |
| D389,244 S | 1/1998 | Dunshee et al. |
| 5,705,551 A | 1/1998 | Sasaki |
| D391,639 S | 3/1998 | Dunshee et al. |
| 5,749,895 A | 5/1998 | Sawyer |
| 5,762,955 A | 6/1998 | Smith |
| 5,782,788 A | 7/1998 | Widemire |
| 5,823,983 A | 10/1998 | Rosofsky |
| 5,823,986 A | 10/1998 | Peterson |
| D402,371 S | 12/1998 | Haynes et al. |
| 5,876,745 A | 3/1999 | Muraoka |
| 5,902,443 A | 5/1999 | Kanakubo |
| 5,928,611 A | 7/1999 | Leung |
| 5,931,800 A | 8/1999 | Rasmussen et al. |
| 5,947,917 A | 9/1999 | Carte |
| 5,951,505 A | 9/1999 | Gilman et al. |
| 5,998,694 A | 12/1999 | Jensen et al. |
| D424,699 S | 5/2000 | Allen |
| 6,093,465 A | 7/2000 | Gilchrist et al. |
| 6,125,265 A | 9/2000 | Yamamoto |
| 6,140,548 A | 10/2000 | Hansen |
| 6,143,352 A | 11/2000 | Clark |
| 6,155,265 A | 12/2000 | Hammerslag |
| 6,183,593 B1 | 2/2001 | Narang |
| 6,217,603 B1 | 4/2001 | Clark |
| 6,238,692 B1 | 5/2001 | Smith |
| 6,245,960 B1 | 6/2001 | Eaton |
| 6,284,941 B1 | 9/2001 | Cox et al. |
| 6,310,166 B1 | 10/2001 | Hickey |
| 6,329,564 B1 | 12/2001 | Lebner |
| 6,352,704 B1 | 3/2002 | Nicholson |
| 6,410,818 B1 | 6/2002 | Oyaski |
| 6,439,789 B1 | 8/2002 | Ballance |
| D463,564 S | 9/2002 | Siegwart et al. |
| 6,455,064 B1 | 9/2002 | Narang |
| 6,479,725 B1 | 11/2002 | Brothers |
| 6,482,431 B2 | 11/2002 | Smith |
| 6,512,023 B1 | 1/2003 | Malofsky |
| D472,319 S | 3/2003 | Oltmann |
| 6,559,350 B1 | 5/2003 | Tetreault |
| 6,579,469 B1 | 6/2003 | Nicholson |
| 6,582,713 B2 | 6/2003 | Newell |
| 6,589,269 B2 | 7/2003 | Zhu |
| 6,595,940 B1 | 7/2003 | Alessio |
| 6,596,917 B2 | 7/2003 | Oyaski |
| 6,599,318 B1 | 7/2003 | Gabbay |
| 6,620,846 B1 | 9/2003 | Jonn et al. |
| 6,632,450 B1 | 10/2003 | Gregory |
| 6,635,272 B2 | 10/2003 | Leaderman |
| 6,652,559 B1 | 11/2003 | Tetreault |
| 6,667,051 B1 | 12/2003 | Gregory |
| 6,712,839 B1 | 3/2004 | Loenne |
| 6,787,682 B2 | 9/2004 | Gilman |
| 6,837,027 B2 | 1/2005 | Hickey |
| 6,942,683 B2 | 9/2005 | Dunshee |
| D520,639 S | 5/2006 | Dodd et al. |
| 7,044,982 B2 | 5/2006 | Milbocker |
| 7,066,934 B2 | 6/2006 | Kirsch |
| 7,122,712 B2 | 10/2006 | Lutri |
| 7,144,390 B1 | 12/2006 | Hannigan |
| 7,164,054 B2 | 1/2007 | Mori |
| D548,348 S | 8/2007 | Nash |
| 7,252,837 B2 | 8/2007 | Guo |
| D562,461 S | 2/2008 | Nash |
| 7,371,400 B2 | 5/2008 | Borenstein |
| D574,962 S | 8/2008 | Atkins et al. |
| D580,553 S | 11/2008 | Nash |
| 7,457,667 B2 | 11/2008 | Skiba |
| D582,561 S | 12/2008 | Sachi |

(56) References Cited

U.S. PATENT DOCUMENTS

| | | |
|---|---|---|
| D584,415 S | 1/2009 | Sachi |
| 7,576,257 B2 | 8/2009 | Lagreca, Sr. |
| D611,156 S | 3/2010 | Dunshee |
| 7,713,463 B1 | 5/2010 | Reah |
| D618,810 S | 6/2010 | Tanigawa et al. |
| 7,943,811 B2 | 5/2011 | Da Silva Macedo, Jr. |
| 7,981,136 B2 | 7/2011 | Weiser |
| 7,982,087 B2 | 7/2011 | Greener |
| D646,789 S | 10/2011 | Barth |
| 8,343,606 B2 | 1/2013 | Marchitto |
| 8,353,966 B2 | 1/2013 | Day et al. |
| D679,098 S | 4/2013 | Ogawa |
| D679,402 S | 4/2013 | Conrad-vlasak |
| D679,403 S | 4/2013 | Heinecke |
| D679,819 S | 4/2013 | Peron |
| D679,820 S | 4/2013 | Peron |
| 8,528,730 B2 | 9/2013 | Grossman |
| D691,730 S | 10/2013 | Smith |
| D692,566 S | 10/2013 | Adoni |
| D693,010 S | 11/2013 | Mosa |
| D694,892 S | 12/2013 | Chan |
| 8,603,053 B2 | 12/2013 | Riesinger |
| D697,216 S | 1/2014 | Chan |
| 8,642,831 B2 | 2/2014 | Larsen et al. |
| 8,663,171 B2 | 3/2014 | Tambourgi |
| D707,829 S | 6/2014 | Chan et al. |
| D708,751 S | 7/2014 | Chan et al. |
| 8,777,986 B2 | 7/2014 | Straehnz |
| D712,045 S | 8/2014 | Thornton |
| D713,967 S | 9/2014 | Adoni |
| 8,884,094 B2 | 11/2014 | Lockwood |
| 9,000,251 B2 | 4/2015 | Murphy |
| RE45,510 E | 5/2015 | Iwahashi et al. |
| D728,803 S | 5/2015 | Sinda et al. |
| 9,119,620 B2 | 9/2015 | Peterson |
| D745,688 S | 12/2015 | Chan et al. |
| D745,689 S | 12/2015 | Chan et al. |
| D746,479 S | 12/2015 | Arefieg |
| D750,789 S | 3/2016 | Mackay et al. |
| D757,950 S | 5/2016 | Karlsson et al. |
| 9,339,417 B2 | 5/2016 | Ogawa |
| 9,381,284 B2 | 7/2016 | Cornet |
| 9,492,171 B2 | 11/2016 | Patenaude |
| 9,623,142 B2 | 4/2017 | Jonn |
| 9,655,622 B2 | 5/2017 | Jonn |
| 2001/0002432 A1 | 5/2001 | Bugge |
| 2001/0028943 A1 | 10/2001 | Mashiko |
| 2001/0037077 A1 | 11/2001 | Wiemken |
| 2002/0018689 A1 | 2/2002 | Badejo |
| 2002/0019652 A1 | 2/2002 | Mannheimer |
| 2002/0037310 A1 | 3/2002 | Jonn |
| 2002/0185396 A1 | 12/2002 | Mainwaring |
| 2002/0192107 A1* | 12/2002 | Hickey ............... A61B 50/30 422/1 |
| 2002/0193721 A1 | 12/2002 | Vandruff |
| 2003/0031499 A1 | 2/2003 | Heard |
| 2003/0093024 A1 | 5/2003 | Falleiros |
| 2003/0100955 A1 | 5/2003 | Greenawalt |
| 2003/0109819 A1 | 6/2003 | Tsuruda |
| 2003/0125654 A1 | 7/2003 | Malik |
| 2003/0175824 A1 | 9/2003 | Pishko et al. |
| 2003/0225355 A1 | 12/2003 | Butler |
| 2004/0001879 A1 | 1/2004 | Guo |
| 2004/0060867 A1 | 4/2004 | Kriksunov et al. |
| 2004/0120849 A1 | 6/2004 | Stewart |
| 2004/0142041 A1 | 7/2004 | Macdonald |
| 2004/0162512 A1 | 8/2004 | Liedtke et al. |
| 2004/0220505 A1 | 11/2004 | Worthley |
| 2005/0015036 A1 | 1/2005 | Lutri |
| 2005/0043820 A1 | 2/2005 | Browning |
| 2005/0085757 A1 | 4/2005 | Santanello |
| 2005/0147457 A1 | 7/2005 | Badejo et al. |
| 2005/0153090 A1 | 7/2005 | Marchitto |
| 2005/0154340 A1 | 7/2005 | Schlussel |
| 2005/0182443 A1 | 8/2005 | Jonn et al. |
| 2005/0208100 A1 | 9/2005 | Weber et al. |
| 2005/0288706 A1 | 12/2005 | Widomski et al. |
| 2006/0058721 A1 | 3/2006 | Lebner |
| 2006/0141012 A1* | 6/2006 | Gingras ............... B32B 38/0008 424/442 |
| 2006/0173394 A1 | 8/2006 | Stroock et al. |
| 2006/0265005 A1 | 11/2006 | Beese |
| 2007/0106195 A1 | 5/2007 | Marcoux |
| 2007/0218101 A1 | 9/2007 | Johnson et al. |
| 2007/0272211 A1 | 11/2007 | Kassner |
| 2007/0299542 A1 | 12/2007 | Mathisen et al. |
| 2008/0051687 A1 | 2/2008 | Rogers |
| 2008/0086113 A1 | 4/2008 | Tenney et al. |
| 2008/0109034 A1 | 5/2008 | Mather et al. |
| 2008/0110961 A1 | 5/2008 | Voegele et al. |
| 2008/0154168 A1 | 6/2008 | Lutri |
| 2008/0167633 A1 | 7/2008 | Vannucci |
| 2008/0280037 A1 | 11/2008 | Sheridan et al. |
| 2008/0302487 A1 | 12/2008 | Goodman |
| 2010/0106120 A1 | 4/2010 | Holm |
| 2010/0262091 A1 | 10/2010 | Larsson |
| 2010/0298791 A1 | 11/2010 | Jones |
| 2011/0047766 A1 | 3/2011 | Mcaulay et al. |
| 2011/0071415 A1 | 3/2011 | Karwoski |
| 2011/0092874 A1 | 4/2011 | Baschnagel |
| 2011/0208102 A1 | 8/2011 | Chawki |
| 2011/0236459 A1 | 9/2011 | Stopek |
| 2011/0253303 A1 | 10/2011 | Miyachi et al. |
| 2012/0220912 A1 | 8/2012 | Shang |
| 2012/0238933 A1 | 9/2012 | Murphy |
| 2012/0277645 A1 | 11/2012 | Kikuta et al. |
| 2013/0012988 A1 | 1/2013 | Blume et al. |
| 2013/0041337 A1 | 2/2013 | Aali |
| 2013/0066365 A1 | 3/2013 | Belson |
| 2013/0084323 A1 | 4/2013 | Riebman et al. |
| 2013/0138068 A1 | 5/2013 | Hu |
| 2013/0143326 A1 | 6/2013 | Tai et al. |
| 2013/0144399 A1 | 6/2013 | Tai et al. |
| 2013/0204077 A1 | 8/2013 | Nagale et al. |
| 2013/0218125 A1 | 8/2013 | Stopek et al. |
| 2013/0245784 A1 | 9/2013 | Tan et al. |
| 2013/0274717 A1 | 10/2013 | Dunn |
| 2013/0317405 A1 | 11/2013 | Ha |
| 2014/0024989 A1 | 1/2014 | Ueda |
| 2014/0107561 A1 | 4/2014 | Dorian |
| 2014/0121649 A1 | 5/2014 | Calco |
| 2014/0141152 A1 | 5/2014 | Sostek |
| 2014/0155916 A1 | 6/2014 | Hodgkinson et al. |
| 2014/0171888 A1 | 6/2014 | Croizat |
| 2014/0221495 A1 | 8/2014 | Coneski |
| 2014/0257348 A1 | 9/2014 | Priewe et al. |
| 2014/0257517 A1 | 9/2014 | Deichmann et al. |
| 2015/0057491 A1 | 2/2015 | Goddard et al. |
| 2015/0209186 A1 | 7/2015 | Abbott |
| 2015/0257938 A1 | 9/2015 | Pensler |
| 2015/0314114 A1 | 11/2015 | La Rosa |
| 2015/0351767 A1 | 12/2015 | Zoll et al. |
| 2015/0366669 A1* | 12/2015 | Bartee ............... A61L 27/18 623/23.5 |
| 2016/0030248 A1 | 2/2016 | Potters |
| 2016/0089145 A1 | 3/2016 | Quintero et al. |
| 2016/0296673 A1 | 10/2016 | Sambusseti |
| 2016/0338836 A1 | 11/2016 | Sonnleitner |
| 2017/0056568 A1 | 3/2017 | Shelton, IV et al. |
| 2017/0056569 A1 | 3/2017 | Vendely et al. |
| 2017/0189159 A1 | 7/2017 | Bartee et al. |
| 2017/0273837 A1 | 9/2017 | Brueckner |
| 2017/0367806 A1 | 12/2017 | Gingras et al. |
| 2018/0085103 A1 | 3/2018 | Quintero et al. |
| 2018/0085259 A1 | 3/2018 | Quintero |
| 2018/0085260 A1 | 3/2018 | Quintero |

FOREIGN PATENT DOCUMENTS

| | | |
|---|---|---|
| CN | 1145462 C | 4/2004 |
| CN | 1671333 A | 9/2005 |
| CN | 102755216 B | 5/2015 |
| EP | 0719529 A1 | 7/1996 |
| EP | 2359782 A1 | 8/2011 |

(56) References Cited

FOREIGN PATENT DOCUMENTS

| | | |
|---|---|---|
| JP | 2002017760 A | 1/2002 |
| JP | 2002/537068 | 11/2002 |
| JP | 1359502 S | 5/2009 |
| JP | 2010057687 A | 3/2010 |
| JP | 2012024253 A | 2/2012 |
| JP | 1571238 S | 3/2017 |
| WO | 0049983 A1 | 8/2000 |
| WO | 2008082444 A2 | 7/2008 |

OTHER PUBLICATIONS

Tissuglu, TissuGlu Surgical Adhesive Patient Information Brochure, Cohera Medical, Inc, 2014, pp. 1-6, page number.

* cited by examiner

SCAFFOLDS FOR JOINING LAYERS OF TISSUE AT DISCRETE POINTS

CROSS REFERENCE TO RELATED APPLICATION

This application is a divisional of co-pending U.S. application Ser. No. 15/467,239 filed Mar. 23, 2017. The complete disclosure of which is hereby incorporated herein by reference for all purposes.

The present disclosure relates to resorbable scaffolds comprising passages that provide discrete fixation points of two layers of tissue to each other with an adhesive, while simultaneously enabling direct contact between layers of tissue being joined.

BACKGROUND

A number of methods exist for joining layers of tissue or closing wounds during surgery, such as for instance during abdominoplasty. In abdominoplasty procedures, layers of tissue can be joined utilizing surgical adhesives instead of suturing or stapling, whereby a layer of surgical adhesive is "sandwiched" between the layers of tissue. One known method of applying surgical adhesives is related to dispensing liquid adhesive on one layer of tissue from a dispenser, and then applying the second layer of tissue on top.

Problems with the known methods of tissue joining relate to (i) lack of uniform dispensing of liquid adhesive between layers of tissue being joined, resulting in variability of thickness of adhesive and (ii) complete separation of layers of tissue being joined by adhesives resulting in slower healing and potentially necrosis.

PCT publication No. WO2008/082444 titled "Articles and Methods for Tissue Repair" discloses a method of medically treating a tissue comprising: directing a transfer device to a tissue surface, the transfer device having associated therewith a patterned array of an adhesive; transferring at least a portion of the patterned array of adhesive from the transfer device to the tissue surface by contact adhesion; moving the transfer device away from the tissue surface; positioning an article to be adhered adjacent at least a portion of the adhesive; and adhering the article to the tissue surface using the adhesive.

U.S. Pat. No. 8,353,966 entitled "Scaffold for Bone and Tissue Repair in Mammals" discloses a tissue scaffold for repair and regeneration of bone hard tissue or muscle, skin, or organ soft tissue, the scaffold comprising: a rigid scaffold body having a scaffold central axis, a scaffold transverse dimension, and a scaffold lengthwise dimension which is greater than the scaffold transverse dimension, the scaffold body having a compressive strength between about 20 and about 250 MPa and comprising: biocompatible inorganic glass fibers each having a fiber transverse dimension and a fiber lengthwise dimension which is at least about 10 times the fiber transverse dimension; and an interconnected porosity constituting between about 10 vol. % and about 35 vol. % of the scaffold body; wherein each of the fibers has a diameter between about 20 and about 5000 microns; wherein at least about 75 vol. % of the fibers are longitudinally co-aligned and lie generally lengthwise of the scaffold central axis, are generally free of helical orientation about the scaffold central axis, and are arranged to define open channels within the scaffold which allow fluid flow into and lengthwise within the scaffold; and wherein the fibers are self-bonded together in that adjacent longitudinally aligned fibers are fused together.

U.S. Pat. No. 6,652,559 entitled "Wound Closure System" discloses a wound closure system for closing a wound on a patient, comprising: an elongated flexible backing strip having opposite ends, first and second surfaces facing away from one another and a length and width sufficient to secure facing edges of the wound in close juxtaposition to one another, said backing strip comprising a first portion disposed between said ends and adapted to overlie the facing edges of said wound, and second and third portions disposed on either side of said first portion and each provided with a predetermined number of spaced-apart perforations extending through said backing strip from said first surface to said second surface, said first portion being free of any aperture extending through said backing strip from said first surface to said second surface; a first pressure-sensitive adhesive coated on at least part of the first surface of said backing strip including said second and third portions thereof, to adhere at least said second and third portions of said backing strip to the patient with the facing edges of said wound in said close juxtaposition; a first protective member removably attached to said backing strip and covering said pressure-sensitive adhesive; and a flowable, moisture-curable surgical adhesive for application into said perforations to strengthen the adhesion of said second and third portions of said backing strip to the patient; whereby after (a) removal of said protective member to expose said pressure-sensitive adhesive, (b) application of said backing strip with the exposed pressure-sensitive adhesive onto said patient to secure the facing edges of said wound in said close juxtaposition, and (c) application of said surgical adhesive into said apertures, said surgical adhesive flows through said perforations and upon curing forms discrete bonding sites cooperating with said backing strip to maintain the facing edges of said wound in said close juxtaposition without the cured adhesive adversely affecting the flexibility of said backing strip, wherein a second protective member having a second pressure-sensitive adhesive coated on one side thereof is removably attached to said backing strip and covers said second surface, said strip being disposed between said first and second protective members, and wherein said second protective member is provided with a corresponding number of perforations registering with the perforations defined in said second and third portions of said backing strip, and being in flow communication therewith.

U.S. Patent Application Publication No. 2013/0012988 entitled "Wound Closure Material" discloses wound closure material with a core of biodegradable material, wherein at least one side of the core of biodegradable material is provided with a multitude of discrete spots of an adhesive and the core of biodegradable material comprises an open cell structure.

U.S. Pat. No. 8,642,831 entitled "Device for Promotion of Hemostasis and/or Wound Healing" discloses a hemostatic matrix material comprising a surface and a plurality of open and interconnected cells, said matrix material comprising gelatine or collagen, wherein the surface of said matrix comprises at least one pharmaceutical composition printed onto said surface in individual and discrete locations, wherein said pharmaceutical composition comprises one or more hemostatic agents.

Synthetic tissue adhesive TissuGlu® Surgical Adhesive by Cohera Medical, Inc. is based on a polyurethane prepolymer and is applied in a spot-like discrete application of the adhesive during abdominoplasty, using a multi-point dispenser.

U.S. Patent Application publication No. 2014/0155916 entitled "Multi-layer Porous Film Material" discloses a surgical implant, comprising: a first porous film layer including a plurality of pores; and a second porous film layer including a plurality of pores, the first and second porous film layers being in a stacked configuration and interconnected to one another at a plurality of attachment points to define at least one void between the first and second porous film layers.

U.S. Patent Application publication No. 2008/0109034 entitled "Controlled Adhesive Locations Facilitating Tissue Remodeling" discloses a surgical implant for adhering two portions of tissue together comprising; a) an implantable matrix having at least one layer and a plurality of openings formed within the at least one layer for tissue growth therethrough; and b) a polymer adhesive about the implantable matrix for adhering the two portions of tissue together, the adhesive polymerizing to adhere the tissue together when the two portions of tissue are brought together.

U.S. Patent Application publication No. 2006/0141012 entitled "Tissue Scaffold" discloses a tissue scaffold comprising: a first film including a plurality of cell openings; and a second film adjacent the first film and including a plurality of cell openings larger than the cell openings of the first film; wherein the cell openings of the first film interconnect with the cell openings of the second film to define pathways extending from the first film to the second film.

U.S. Patent Application publication No. 2013/0204077 entitled "Surgical Scaffolds" discloses a surgical scaffold for soft tissue repair, said surgical scaffold comprising a sheet of non-filamentous polymeric material, at least a portion of the sheet surface comprising a plurality of through-holes.

There continues to be a need for improved devices, systems, and methods for joining layers of tissue at discrete points enabling tissue layers being joined to establish contact between each other. There is a need in improved joining of tissues with adhesives, particularly improved devices and methods of delivering the adhesive in a layer with a uniform thickness. Additionally, there is a need in methods and devices which will provide faster tissue healing and joining and preventing tissue necrosis in the areas immediately adjacent the adhesive joint.

SUMMARY OF THE INVENTION

In one embodiment, a device for joining two layers of tissue, comprises a substantially flat and flexible scaffold having an upper surface, a lower surface and sidewalls; a plurality of first passages penetrating said scaffold from said upper surface to said lower surface; a plurality of second passages penetrating said scaffold from said upper surface to said lower surface; a substantially flat and flexible top cover releasably attached to said upper surface and covering all of said upper surface; said top cover having a plurality of top cover passages aligned with said first plurality of passages.

According to another embodiment, there is provided a kit, comprising the device for joining two layers of tissue, a container containing a polymerizable or cross-linkable fluid adhesive, and a dispenser adapted to dispense said adhesive onto said device.

According to yet another embodiment, there is provided a method of adhesively joining layers of tissue, using the device, comprising the steps of: Dispensing a fluid adhesive onto the top cover and filling the plurality of first passages with the adhesive; Removing the top cover from the scaffold; Positioning the scaffold between a first tissue and a second tissue and establishing contact of the adhesive in the first passages with the first and the second tissue; Polymerizing and/or cross-linking the adhesive in contact with the first and second tissue, thus bonding the first and second tissue to each other through the scaffold at discrete points of bonding; Establishing direct contact between the layers of tissue through the plurality of second passages; Leaving the scaffold between the first and the second tissues.

DETAILED DESCRIPTION

Figure 1:
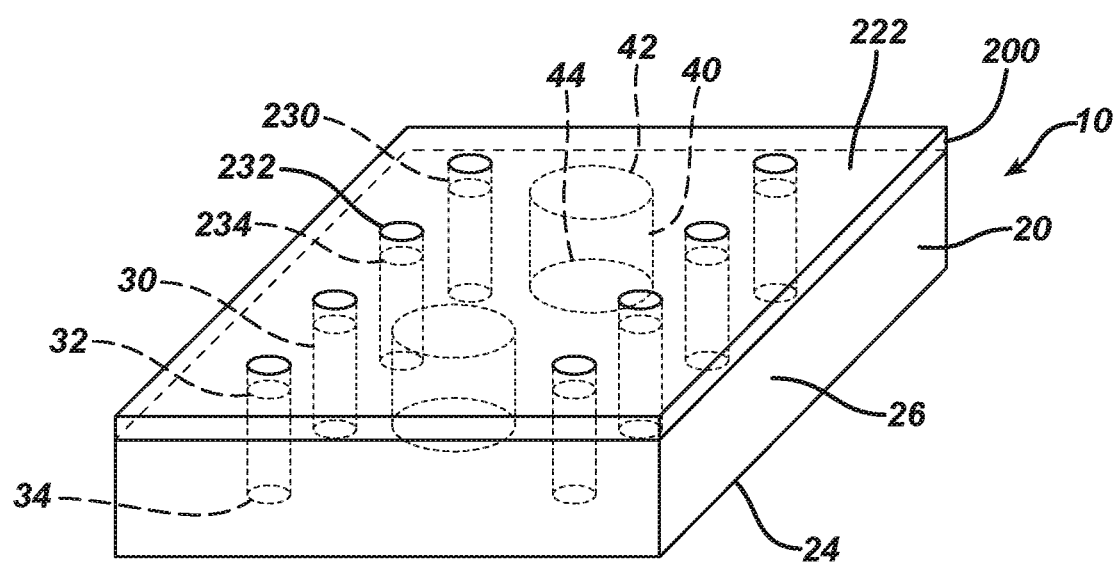
FIG. 1 shows an embodiment of the device in a schematic perspective view.
Figure 2:
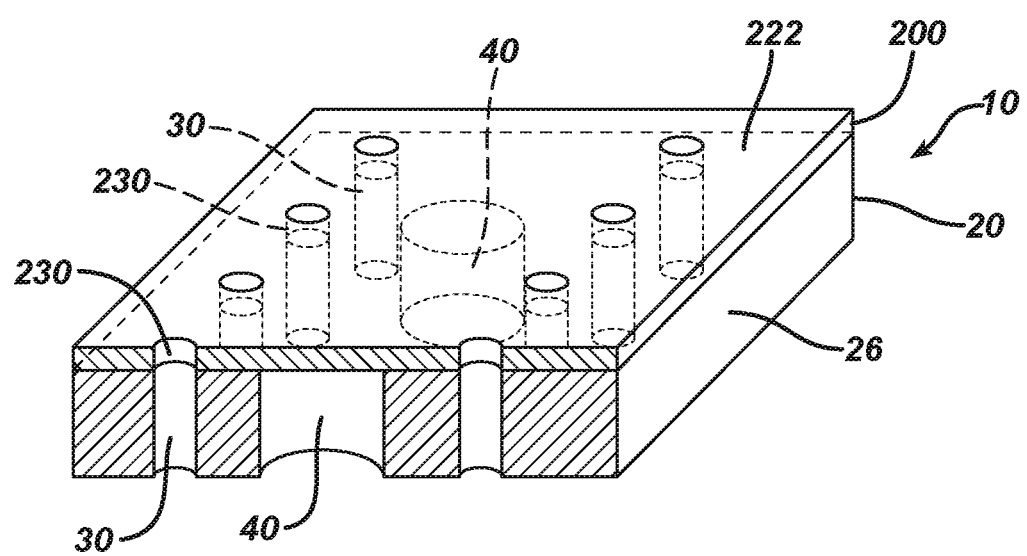
FIG. 2 shows an embodiment of the device in a schematic perspective cross-sectional view.
Figure 3:
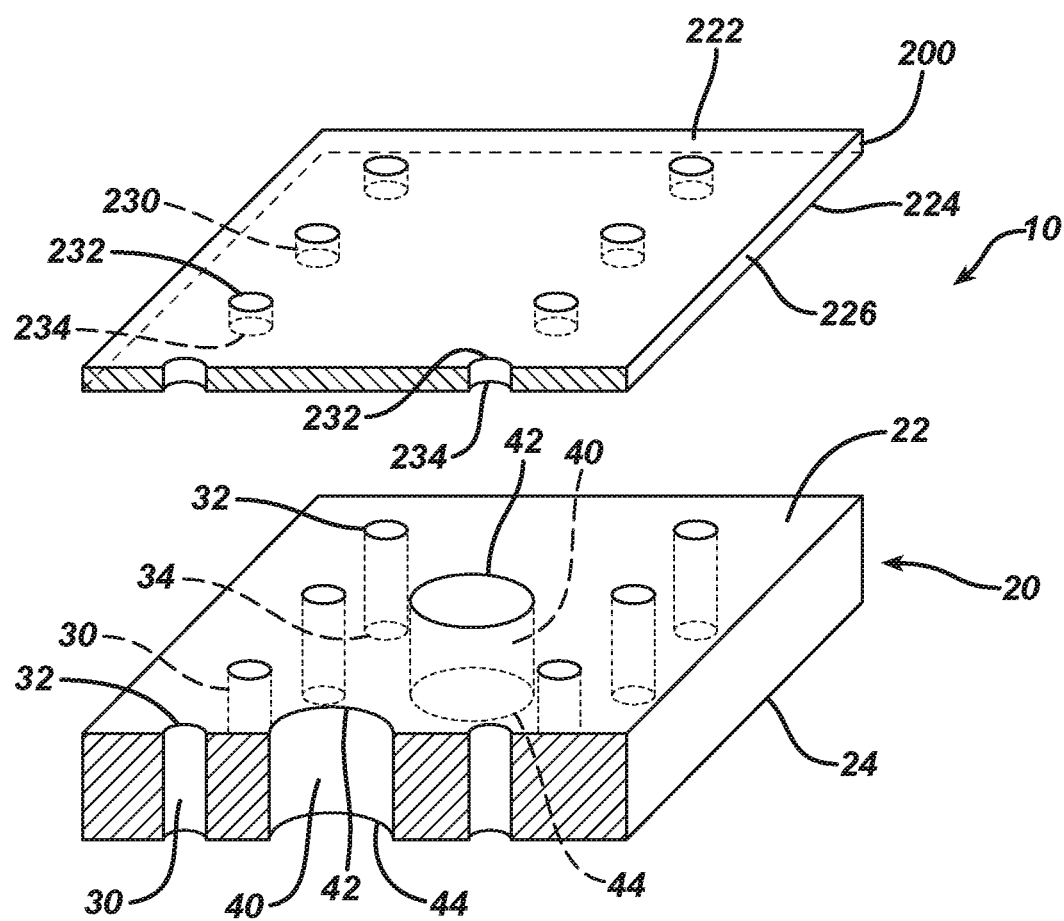
FIG. 3 shows an embodiment of the device in a schematic perspective cross-sectional exploded view.

Referring now to FIGS. 1 through 3, an embodiment of device 10 of the present invention is shown. FIG. 1 is showing a schematic perspective view. FIG. 2 is showing a schematic perspective cross-sectional view, FIG. 3 is showing a schematic perspective cross-sectional exploded view of device 10.

Scaffold

Device 10 comprises thin, flat, flexible scaffold 20 made of resorbable or non-resorbable material. In a preferred embodiment, scaffold 20 is made of at least partially resorbable or at least partially soluble polymeric or composite material. In the most preferred embodiment, scaffold 20 is fully resorbable or fully soluble. Scaffold 20 is substantially flat and flexible and is defined by upper surface 22, lower surface 24 and side walls 26. A plurality of first passages 30 and a plurality of second passages 40 comprise through-holes or apertures in scaffold 20 and traverse scaffold 20 from upper surface 22 to lower surface 24, generally perpendicularly to upper surface 22 and lower surface 24.

First passages 30 are seen on upper surface 22 as first upper openings 32 and are seen on lower surface 24 as first lower openings 34. Second passages 40 are seen on upper surface 22 as second upper openings 42 and are seen on lower surface 24 as second lower openings 44.

In a preferred embodiment, walls of first passages 30 and second passages 40 are perpendicular to upper surface 22 and lower surface 24, i.e. first upper openings 32 have the same dimensions as first lower openings 34; and second upper openings 42 have the same dimensions as second lower openings 44.

In some embodiments (not shown), first passages 30 have conical shape, whereby first upper openings 32 are larger than first lower openings 34.

In a preferred embodiment, second passages 40 are empty openings or apertures. Optionally, second passages 40 can be filled by rapidly soluble materials (not shown), optionally containing medically useful agents, such as wound healing agents, fluid absorbent materials, etc.

Figure 19:
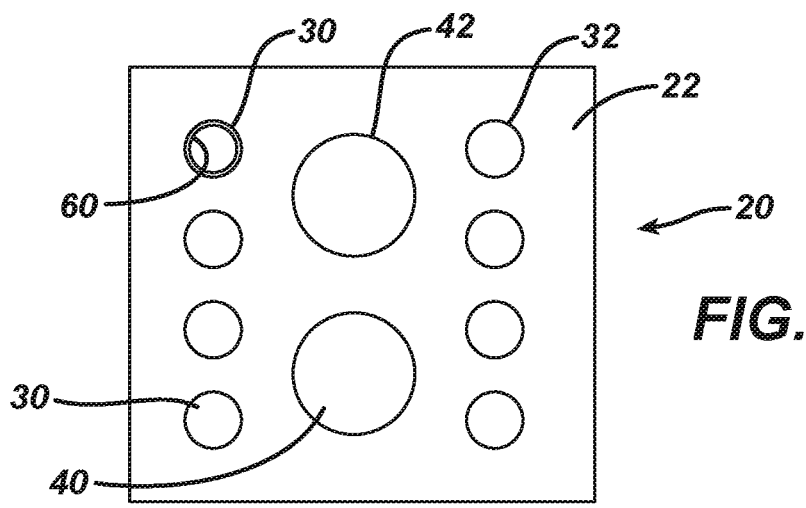
FIGS. 19-21 show embodiments of the scaffold in a schematic top view.
Figure 20:
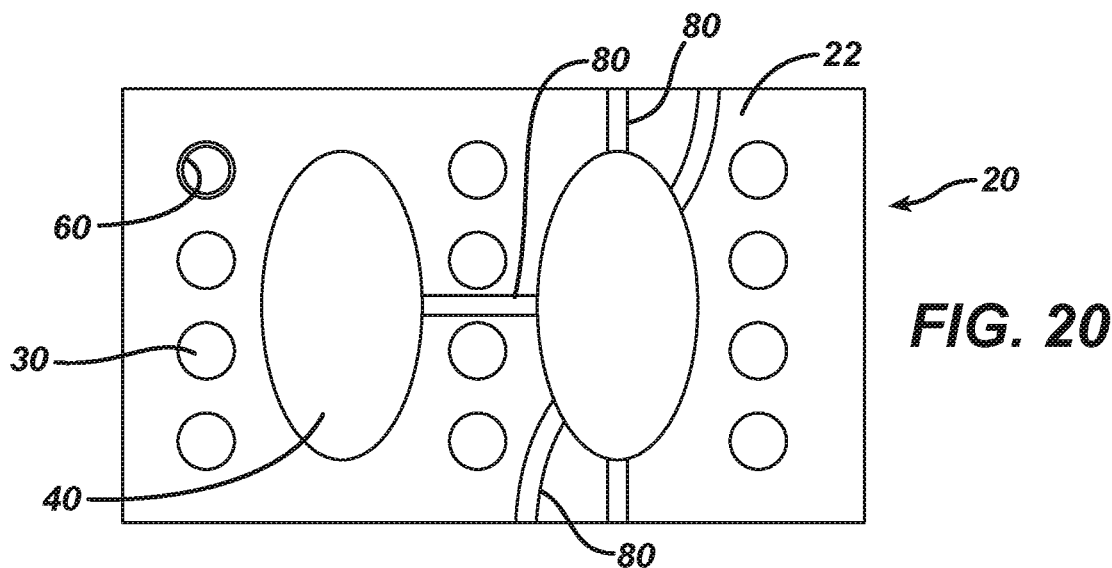
Figure 21:
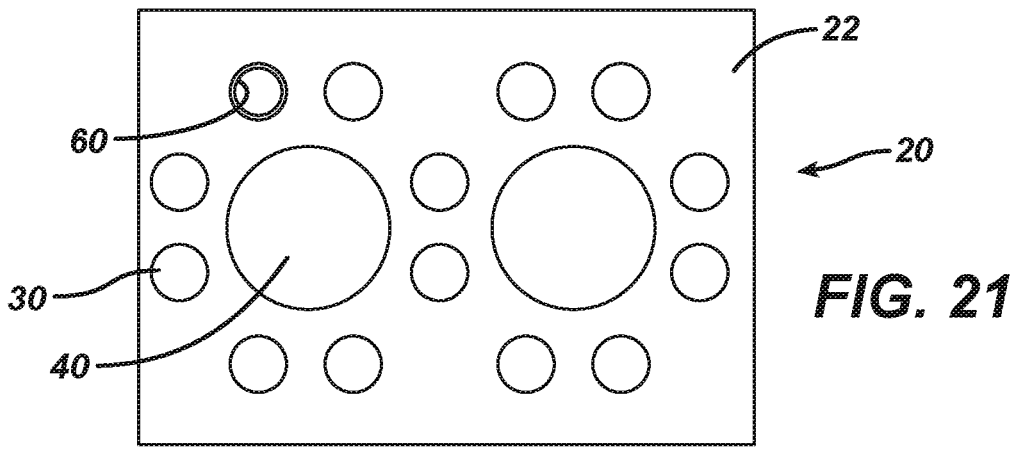

Scaffold 20 can be of any geometrical shape or form, such as square, rectangular, round, oval, triangular etc. Optionally, the scaffold can be trimmable. Thickness of scaffold 20 (or height of sidewalls 26) is from about 0.2 mm to about 8 mm, more preferably from 1 mm to 6 mm, such as 1, 2, 3, 4 mm. The gross surface area of scaffold 20 when measured from a top view as for instance shown in FIGS. 19-21, is from about 3 $cm^2$ to about 400 $cm^2$, more preferably from 5 $cm^2$ to 300 $cm^2$, such as 10, 20, 50, 100, 150, 200 $cm^2$. In some embodiments, when scaffold 20 is substantially circular, the diameter of the circle is from about 2 cm to about 20 cm, such as 5 cm, 10 cm, 15 cm, 20 cm. In some embodiments, when scaffold 20 is substantially square, the side of the square is from about 2 cm to about 20 cm, such as 3, 5, 10, 15, 20 cm.

First and second passages 30, 40, can be of any geometry, including circular, rectangular, etc. When circular, first passages 30 can have diameters from about 1 mm to about 15 mm, such as 2, 5, 10 mm. When circular, second passages 40 can have diameters from about 2 mm to about 50 mm, such as 2, 5, 10, 25, 40 mm. Plurality of second passages 40 can take 50%-95% of space on upper 22 and lower 24 surfaces of scaffold 20 which is not taken by first passages 30, with positioning of second passages 40 configured so as to not intersect any first passages 30. The portion of total area of space on upper 22 and lower 24 surfaces of scaffold 20 taken by first passages 30 can be from 5% to 50%; the portion of total area of space on upper 22 and lower 24 surfaces of scaffold 20 taken by second passages 40 can be from 50% to 95%.

In all embodiments first passages 30 and second passages 40 are covering a substantial portion of scaffold 20, such as 30% to 95% of upper surface 22, such as 40, 60, 80, 90% of upper surface 22. Preferably, surface area taken by second passages 40 is from about 30% to about 300% of the surface area taken by first passages 30. Preferably, surface area taken by second passages 40 is equal or larger than surface area taken by first passages 30.

Scaffold 20 can have from 4 to hundreds of first passages 30, such as 10, 20, 50, 75, 100, 500. Scaffold 20 can have from 1 to hundreds of second passages 40, such as 1, 5, 10, 20, 50, 100.

Scaffold 20 can be manufactured by many techniques known to a skilled artisan, such as punching, laminating, web converting, injection molding, layers bonding, machining, 3D printing, etc., and combinations thereof.

Scaffold 20 may be formed of either synthetic, semi-synthetic, or natural materials or combinations thereof. In particular, suitable materials include, for example, PLGA or poly(lactic-co-glycolic acid, polylactic acid, polyglycolic acid, polycaprolactone, nylon, polyolefin, polyethylene, polypropylene, ethylene propylene copolymers, and ethylene butylene copolymers, polyurethanes, polyurethane foams, polystyrenes, plasticized polyvinylchlorides, polyesters, polyamides, copolymers and mixtures of the above, cotton, collagen, gelatin, and composites of the above. Scaffold 20 can be porous or non-porous.

Scaffold 20 may be either biodegradable, or not biodegradable, or partially biodegradable. By "biodegradable" it is meant that scaffold 20 biodegrades over time in vivo, such that it does not require physical removal after a set period of time. Thus, for example, a biodegradable material is one that, in the in vivo environment, will biodegrade over a period of from about one week to about five years. A non-biodegradable material is one that does not biodegrade in an in vivo environment within about five years.

In one embodiment, there are provided surface grooves 80 connecting at least some of second passages 40 each other and/or to periphery of scaffold 20 as shown in FIG. 20. Surface grooves 80 are cut into upper surface 22 and/or lower surface 24 and are not in fluid communication with first passages 30. Surface grooves 80 are enabling bodily fluids movement or drainage from the area of joining tissues T1 and T2 with bodily fluids moving around discrete joining bonding points formed by adhesive 70.

Top Cover

Device 10 further comprises top cover 200 which comprises thin, flat, flexible film defined by upper surface 222, lower surface 224 and side walls 226. Top cover 200 is releasably attached to upper surface 22 and is configured to cover at least all upper surface 22 as shown in FIGS. 1-3. In alternative embodiments, top cover 200 extends beyond upper surface 22 and is larger than upper surface 22. Top cover 200 has a plurality of top cover passages 230 which comprise through-holes or apertures in top cover 200 and traverse top cover 200 from its upper surface 222 to its lower surface 224, generally perpendicularly to upper surface 222 and lower surface 224. Top cover passages 230 are seen on upper surface 222 as top cover upper openings 232 and are seen on lower surface 224 as top cover lower openings 234.

In a preferred embodiment, walls of top cover passages 230 are perpendicular to top cover 200 upper surface 222 and lower surface 224, i.e., top cover upper openings 232 have the same dimensions as top cover lower openings 234; In some embodiments (not shown), top cover passages 230 have conical shape, whereby top cover upper openings 232 are larger than top cover lower openings 234.

Alignment

First passages 30 are in registration with top cover passages 230, i.e., when top cover 200 is positioned on scaffold 20 as shown in FIGS. 1-2, first passages 30 are aligned with top cover passages 230, forming through-holes or apertures going all the way from top cover 200 upper surface 222 to scaffold 20 lower surface 24. As shown, first upper openings 32 are aligned or are in registration with top cover lower openings 234.

First upper openings 32 can be of the same or different dimensions as top cover lower openings 234. In a preferred embodiment, as shown, first upper openings 32 have the same dimensions as top cover lower openings 234. In some embodiments, first upper openings 32 are smaller than top cover lower openings 234 (not shown). In some embodiments, first upper openings 32 are larger than top cover lower openings 234 (not shown).

Second passages 40 are completely covered by top cover 200 and are not exposed on top cover 200 upper surface 222, i.e. second upper openings 42 are fully covered by top cover 200.

Top cover 200 is made of any polymeric material, such as polymeric film, release liner, etc. material.

Embodiment with Optional Bottom Cover

Figure 4:
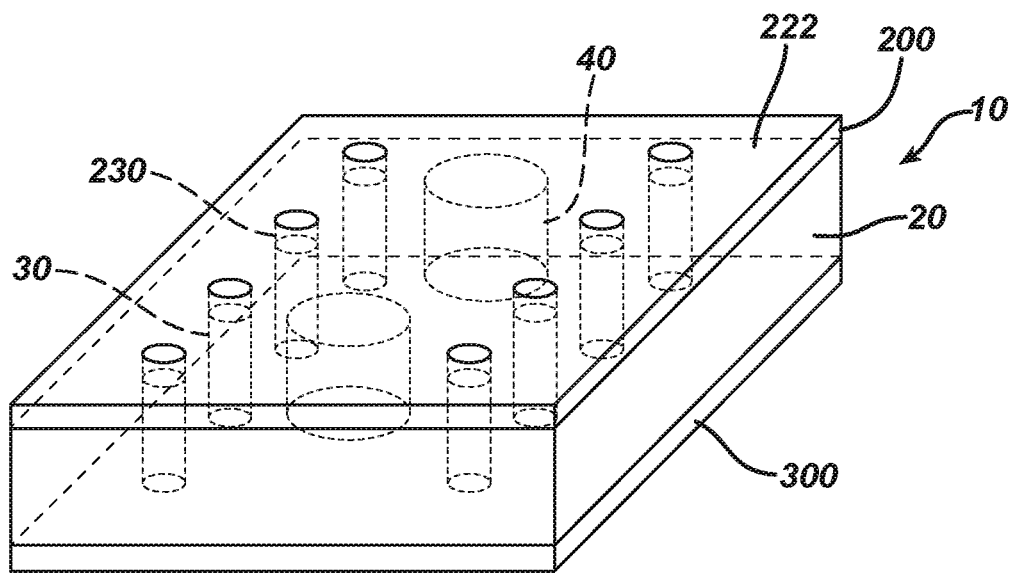
FIG. 4 shows an embodiment of the device in a schematic perspective view.
Figure 5:
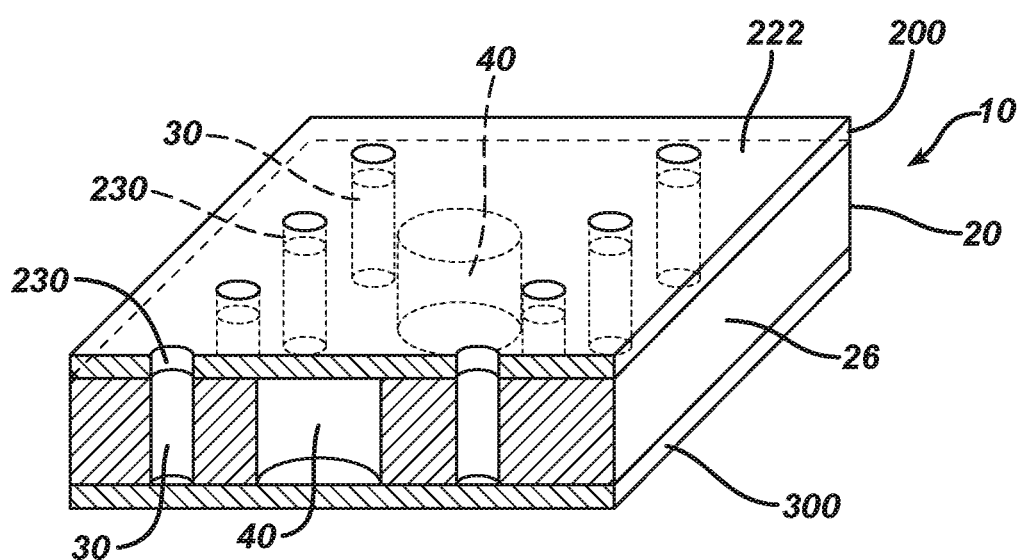
FIG. 5 shows an embodiment of the device in a schematic perspective cross-sectional view.
Figure 6:
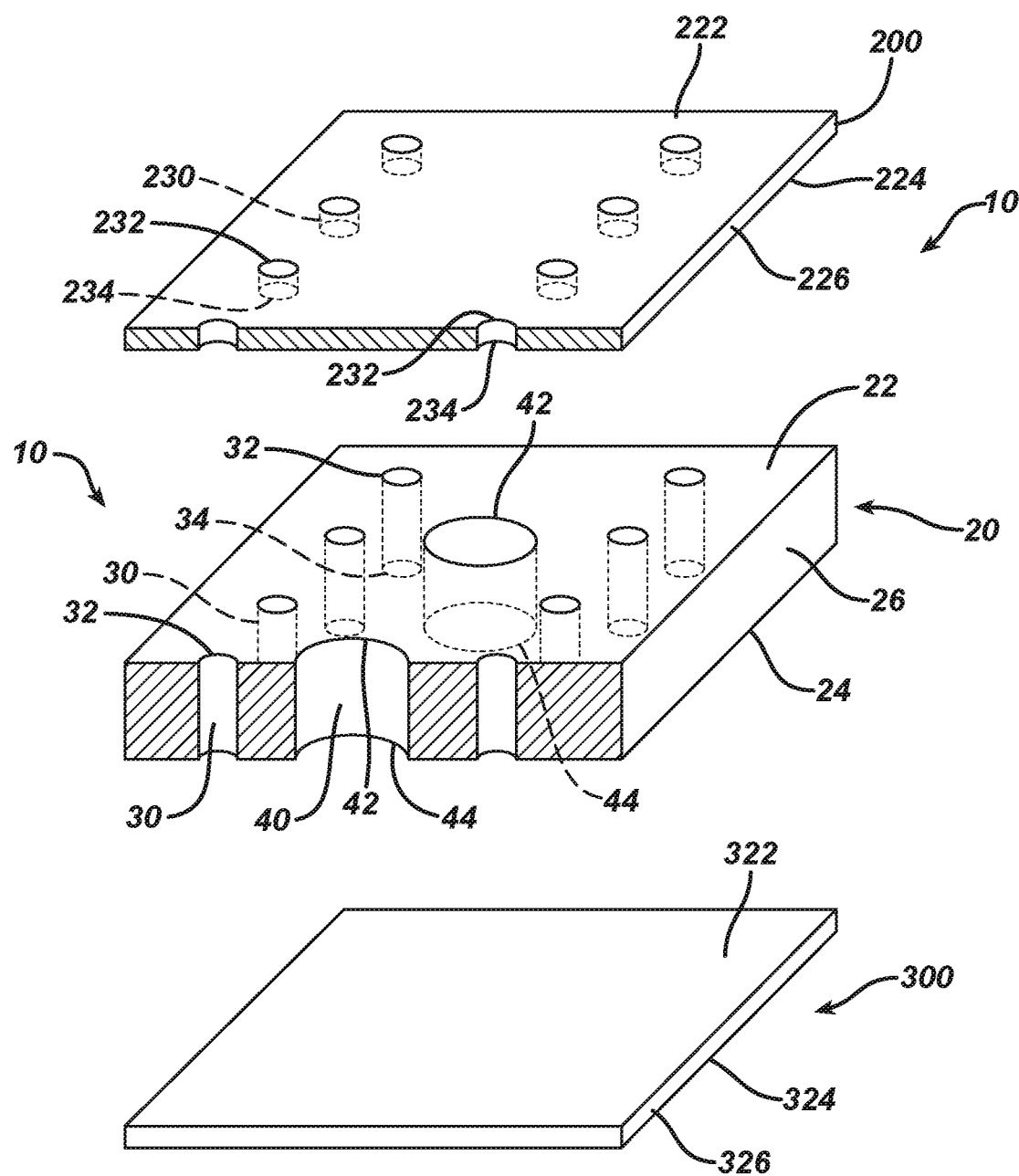
FIG. 6 shows an embodiment of the device in a schematic perspective cross-sectional exploded view.

Referring now to FIGS. 4 through 6, an embodiment of device 10 of the present invention is shown, which is similar to the embodiments of FIGS. 1-3, but with an additional optional bottom cover 300. FIG. 4 is showing a schematic perspective view, FIG. 5 is showing a schematic perspective cross-sectional view, FIG. 6 is showing a schematic perspective cross-sectional exploded view of device 10. The advantages of the bottom cover include improved handling and ease of use capabilities of the device as hereinafter described, for example, in the section describing "indirect fill", below.

In this embodiment, device 10 further comprises optional bottom cover 300 which comprises thin, flat, flexible film defined by upper surface 322, lower surface 324 and side walls 326. Bottom cover 300 is releasably attached to lower surface 24 of scaffold 20 and is configured to cover at least all lower surface 24 as shown in FIGS. 1-3. In alternative embodiments, bottom cover 300 extends beyond lower surface 24 and is larger than lower surface 24.

Optional bottom cover 300 has no apertures or openings, and is configured to completely cover first passages 30 and second passages 40, i.e., to cover first lower openings 34 and second lower openings 44.

Bottom cover 300 is made of any polymeric material, such as polymeric film, release liner, etc. material.

Pull Tab

Figure 7:
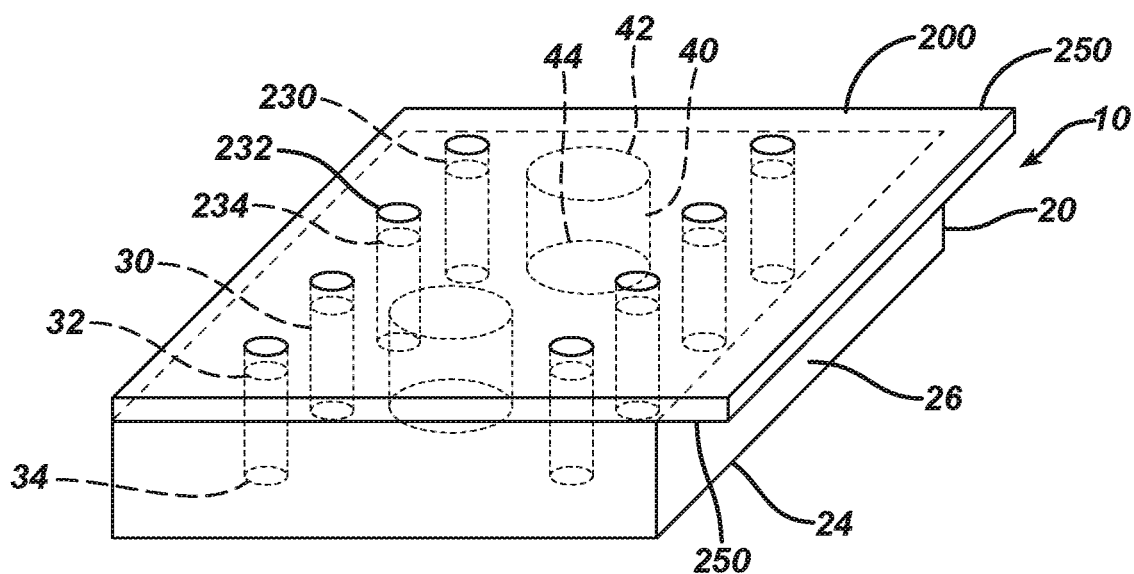
FIG. 7 shows an embodiment of the device in a schematic perspective view.
Figure 8:
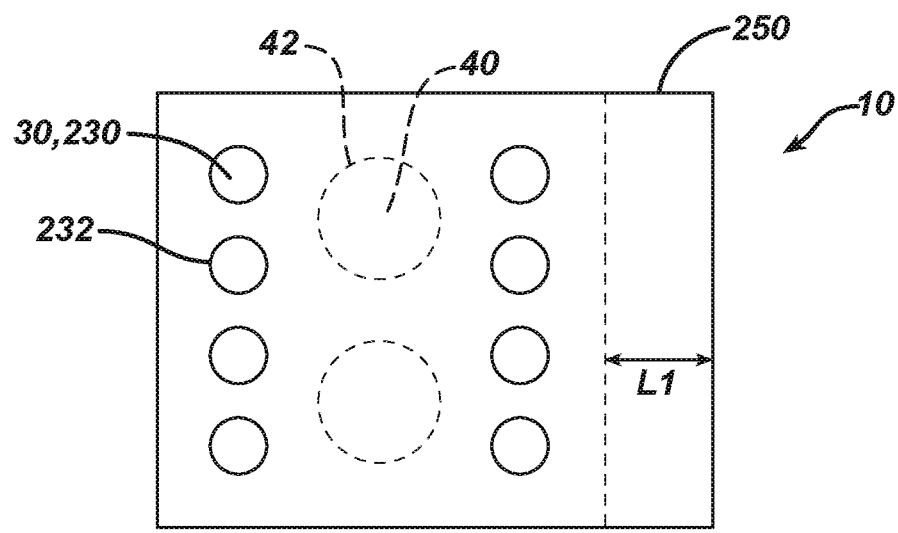
FIG. 8 shows an embodiment of the device in a schematic top view.
Figure 9:
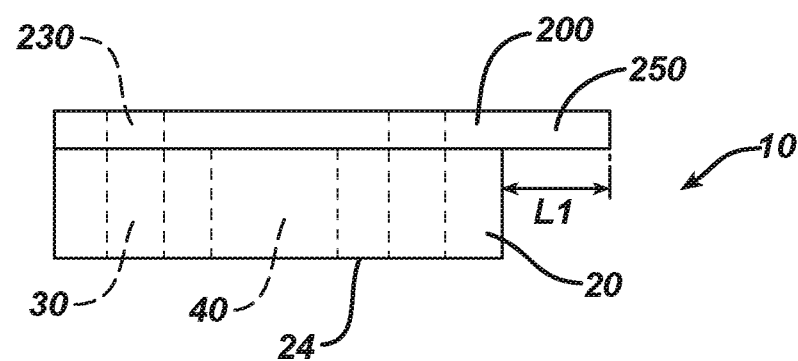
FIG. 9 shows an embodiment of the device in a schematic side view.

Referring now to FIGS. 7-9, an embodiment of device 10 is shown with top cover 200 having a top cover pull tab 250. FIG. 7 is showing a schematic perspective view, FIG. 8 is showing a schematic top view, FIG. 9 is showing a schematic side view of device 10.

Top cover pull tab 250 extends beyond scaffold 20 and overhangs scaffold 20 to facilitate lift-up and removal of releasable top cover 200. Top cover pull tab 250 is sized to be easily graspable by hand or by surgical grasper or by another surgical tool and can have a width substantially identical to top cover 200 width (as shown) or can be narrower, with the width of top cover pull tab 250 being 10%-80% of the width of top cover 200. In some embodiments, width of top cover pull tab 250 is 1-10 cm, such as 1, 2, 3, 4, 5 cm. Length L1 of top cover pull tab 250 indicated in FIGS. 8-9, 11-12 by arrow L1 is from about 3 mm to about 30 mm, such as 5, 10, 15, 20 mm.

Figure 10:
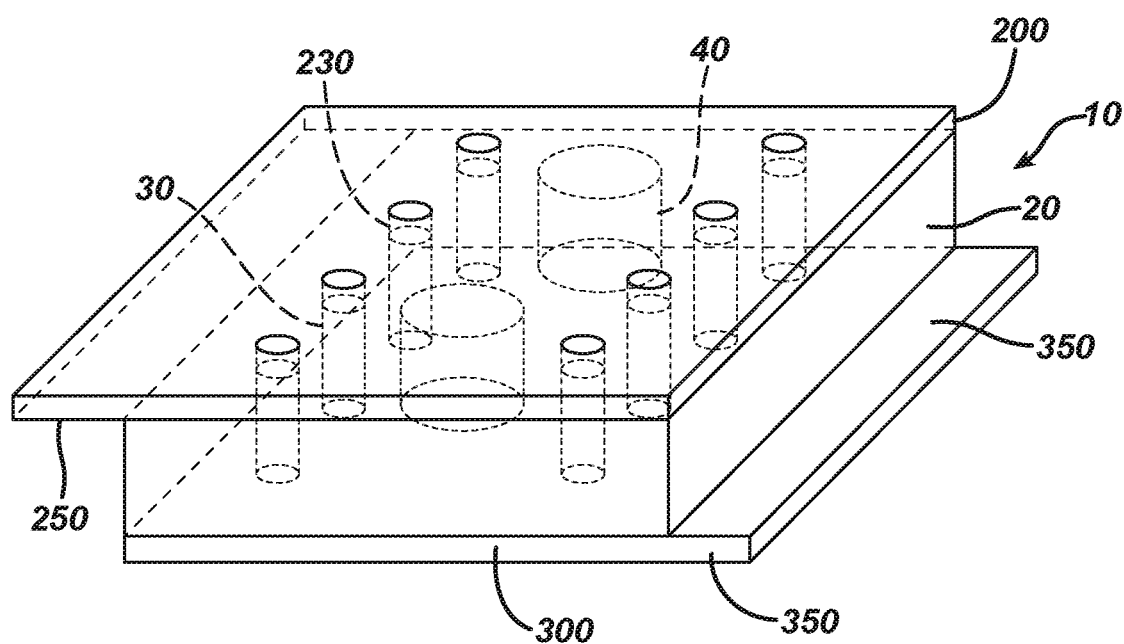
FIG. 10 shows an embodiment of the device in a schematic perspective view.
Figure 11:
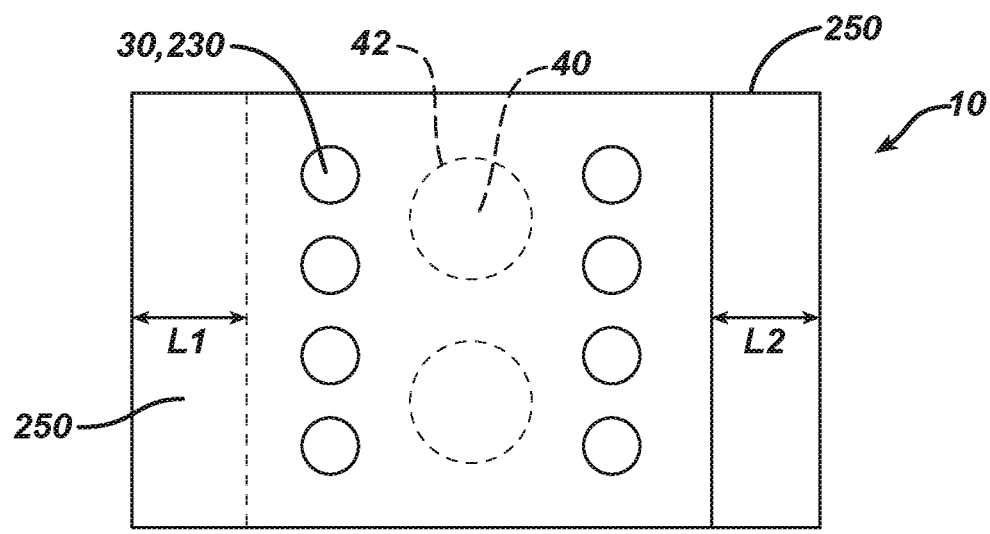
FIG. 11 shows an embodiment of the device in a schematic top view.
Figure 12:
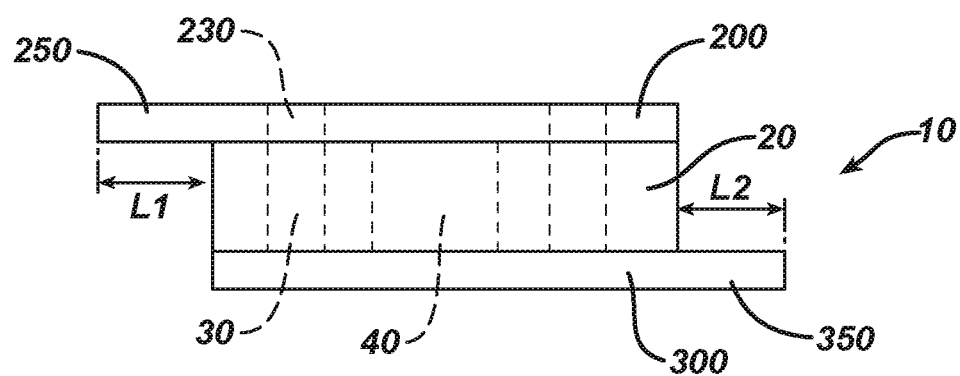
FIG. 12 shows an embodiment of the device in a schematic side view.

Referring now to FIGS. 10-12, an embodiment of device 10 is shown with top cover 200 having a top cover pull tab 250, and bottom cover 300 having a bottom cover pull tab 350.

FIG. 10 is showing a schematic perspective view, FIG. 11 is showing a schematic top view, FIG. 12 is showing a schematic side view of device 10. Bottom cover pull tab 350 extends beyond scaffold 20 and overhangs scaffold 20 to facilitate lift-up and removal of releasable bottom cover 300. Bottom cover pull tab 350 is sized to be easily graspable by hand or by surgical grasper or by another tool and can have a width substantially identical to bottom cover 300 width (as shown) or can be narrower, with the width of bottom cover pull tab 350 being 10%-80% of the width of bottom cover 300. In some embodiments, width of bottom cover pull tab 350, is 1-10 cm, such as 1, 2, 3, 4, 5 cm. Length L2 of bottom cover pull tab 350 indicated in FIGS. 11-12 by arrow L2 is from about 3 mm to about 30 mm, such as 5, 10, 15, 20 mm.

As shown in FIGS. 10-12, top cover pull tab 250, and bottom cover pull tab 350 can be opposite each other for ease of independent removal of top cover 200 and bottom cover 300. In alternative embodiments (not shown) top cover pull tab 250, and bottom cover pull tab 350 can be positioned over the same sides of scaffold 20, or can be positioned over adjacent sides of scaffold 20.

Additional Embodiment Top and Cross-Sectional Views

Figure 13:
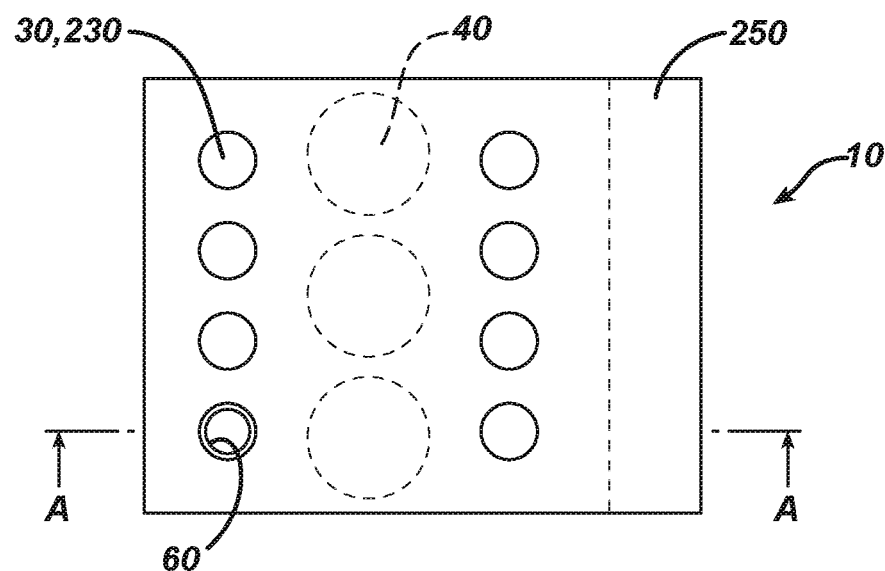
FIG. 13 shows an embodiment of the device in a schematic top view.
Figure 14:
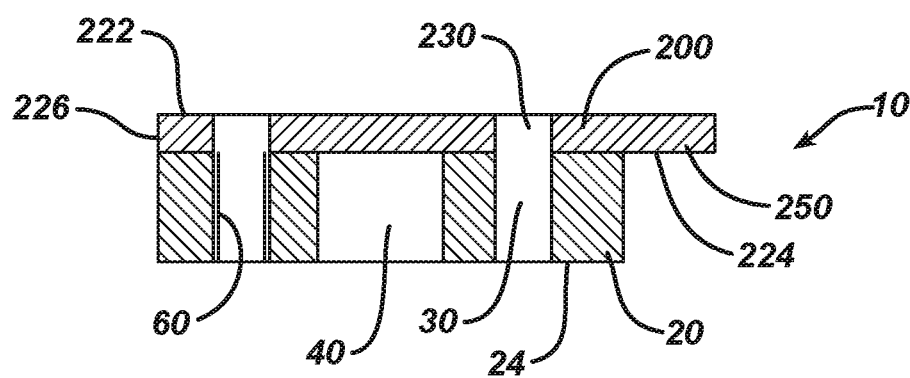
FIG. 14 shows an embodiment of the device in a schematic side cross-sectional view.

Referring now to FIGS. 13 and 14, an embodiment of device 10 similar to embodiments of FIGS. 7-9 is shown, with the shown embodiment having three of second passages 40 instead of two. FIG. 13 shows a schematic top view, and FIG. 14 shows a schematic side cross-sectional view along the lines A-A indicated in FIG. 13.

Figure 15:
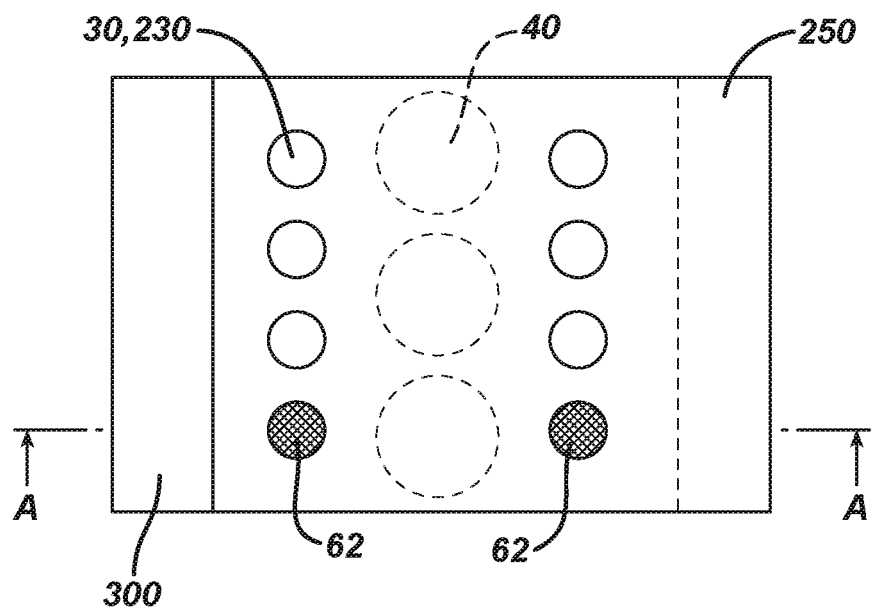
FIG. 15 shows an embodiment of the device in a schematic top view.
Figure 16:
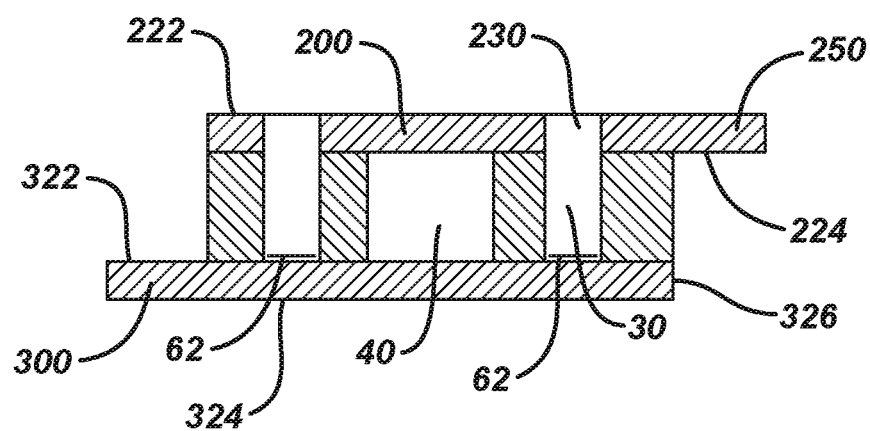
FIG. 16 shows an embodiment of the device in a schematic side cross-sectional view.

Referring now to FIGS. 15 and 16, an embodiment of device 10 similar to embodiments of FIGS. 10-12 is shown, with the shown embodiment having three second passages 40 instead of two. FIG. 15 shows a schematic top view, and FIG. 16 shows a schematic side cross-sectional view along the lines A-A indicated in FIG. 15.

PSA

Figure 17:
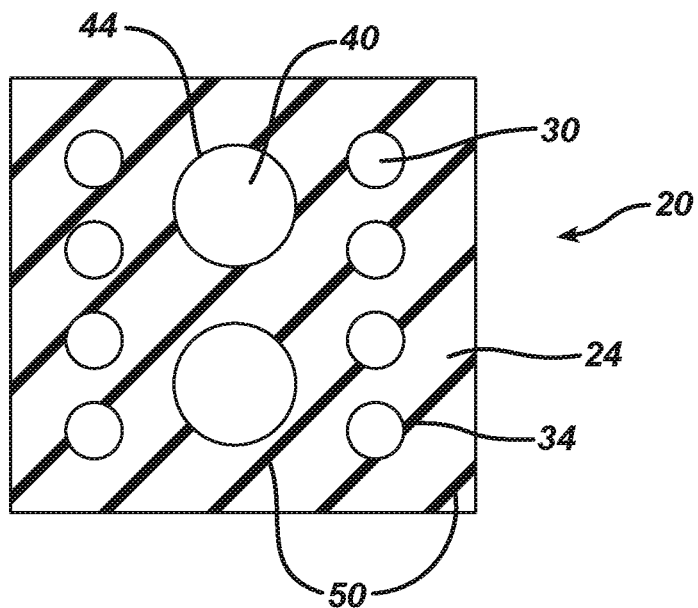
FIGS. 17-18 show embodiments of the scaffold in a schematic bottom view.
Figure 18:
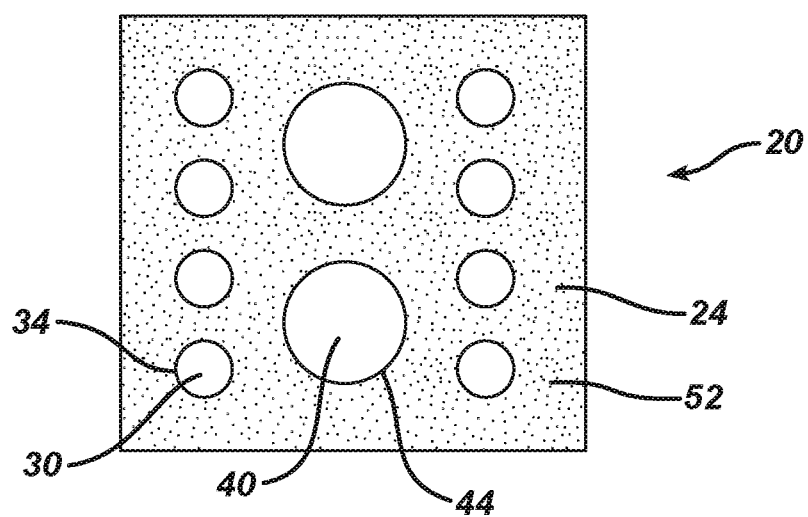

Referring now to FIGS. 17 and 18, an embodiment of scaffold 20 similar to embodiments of FIGS. 1-12 is shown, with FIGS. 17 and 18 showing a schematic bottom view, i.e., view from the lower surface 24. FIG. 17 shows optional pressure sensitive adhesive bands or stripes 50 disposed over lower surface 24, covering from 10% to 90% of lower surface 24 area not taken by first passages 30 and second passages 40, i.e. covering from 10% to 90% of lower surface 24 area not taken by first lower openings 34 and second lower openings 44. In some embodiments, optional pressure sensitive adhesive stripes 50 are covering 20, 30, 40, 50, 60, or 70% of lower surface 24 area not taken by first passages 30 and second passages 40. Other shapes and forms of applying pressure sensitive adhesive are contemplated, including dots, squares, mixed angular bands, etc.

FIG. 18 shows, in an alternative embodiment, optional pressure sensitive 52 disposed over lower surface 24, covering 100% of lower surface 24 area not taken by first passages 30 and second passages 40.

Optionally (not shown), pressure sensitive adhesive can be additionally or alternatively deployed on upper surface 22 of scaffold 20, in stripes, dots, bands, or in full coverage, in all cases on surface not taken by first passages 30 and second passages 40.

Initiator

Referring now to FIGS. 19-21, showing a schematic top view, various embodiments of scaffold 20 are shown, with different sizes and different arrangements of first passages 30 and second passages 40.

In a preferred embodiment, initiators and/or accelerators of adhesive polymerization or cross-linking can be disposed in first passages 30 as shown by reference numeral 60, such as by being coated on first passages 30 walls as shown in FIGS. 19-21 and FIGS. 13-14. Initiators and/or accelerators of adhesive polymerization or cross-linking can be also disposed in second passages 40, however in a preferred embodiment, no initiators and/or accelerators of adhesive polymerization or cross-linking are disposed in second passages 40.

In an alternative embodiment, initiators and/or accelerators of adhesive polymerization or cross-linking can be disposed in first passages 30 on bottom cover 300 upper surface 322, either on the whole upper surface 322, or only inside first passages 30 on bottom cover 300 upper surface 322, as shown in FIGS. 15-16 by reference numeral 62.

In one embodiment, initiators and/or accelerators of adhesive polymerization or cross-linking can be disposed in first passages 30 on bottom cover 300 upper surface 322 and also coated on the walls of first passages 30.

In one embodiment (not shown) there is a mesh coated with initiators and/or accelerators of adhesive polymerization or cross-linking provided on upper surface 22, lower surface 24, or both, with the mesh positioned over first passages 30.

Scaffold 20 in some embodiments includes one or more chemical materials located in or on it. For example, one or more chemical substances may be dispersed in or on scaffold 20, preferably within first passages 30, on bottom cover 300 upper surface 322, such as being chemically bound, physically bound, coated, absorbed, or adsorbed to it. Thus, for example, the scaffold 20 preferably includes at least a polymerization initiator or rate accelerator or modifier, and may optionally include one or more bioactive materials.

For example, a polymerization initiator or accelerator or rate modifier may be loaded in or on scaffold 20 so that the initiator or rate modifier provides the desired initiation or rate modification effect to a subsequently applied polymerizable adhesive composition. The polymerization initiator or rate modifier may be immobilized in or on scaffold 20, so that the initiator or rate modifier does not become detached from scaffold 20 and its residues are dispersed in the resultant polymeric material. Alternatively, for example, the polymerization initiator or rate modifier may be initially attached to scaffold 20, but only in such a manner that it becomes mobilized or solubilized by a subsequently applied polymerizable adhesive composition and dispersed in the resultant polymeric material.

If desired, a combination of chemical substances may also be provided in or on scaffold 20, to provide multiple effects. For example, a first chemical species (such as a polymerization initiator or rate modifier) may be immobilized in or on scaffold 20, while a second, different chemical species (such as a bioactive material) may be detachably attached to scaffold 20. Other combinations of chemical species and resultant effects are also envisioned.

The chemical substance may be applied in a uniform manner to scaffold 20, such that there is a substantially uniform concentration of the chemical substance within scaffold 20. Alternatively, the chemical substance may be applied such that a concentration gradient exists across or through scaffold 20.

When present in or on scaffold 20, the chemical substances (i.e., polymerization initiator, rate modifier, and/or bioactive materials, or other additives), may be incorporated in or on scaffold 20 in any suitable manner. For example, the chemical substance may be added to scaffold 20 by contacting scaffold 20 with a solution, mixture, or the like including the chemical substances. The chemical substance may be added to scaffold 20, for example, by dipping, spraying, roll coating, gravure coating, brushing, vapor deposition, or the like. Alternatively, the chemical substance may be incorporated into or onto scaffold 20 during manufacture of scaffold 20, such as during molding.

The polymerization initiator or rate modifier loaded in or on scaffold 20 may provide a number of advantages for example, so as to provide faster polymerization time. The concentration of polymerization initiator or rate modifier may be increased to provide even faster polymerization time.

Because the polymerization initiator or rate modifier is loaded directly in or on scaffold 20, it is not necessary to mix the polymerizable adhesive composition with a polymerization initiator or rate modifier prior to application. This may allow a longer working time, where the polymerizable monomer composition may be more precisely and carefully applied over a longer period of time.

Such suitable initiators are known in the art and are described, for example, in U.S. Pat. Nos. 5,928,611 and 6,620,846, both incorporated herein by reference in their entireties, and U.S. Patent Application No. 2002/0037310, also incorporated herein by reference in its entirety. Quaternary ammonium chloride and bromide salts useful as polymerization initiators are particularly suitable. By way of example, quaternary ammonium salts such as domiphen bromide, butyrylcholine chloride, benzalkonium bromide, acetyl choline chloride, among others, may be used.

Benzalkonium or benzyltrialkyl ammonium halides such as benzyltrialkyl ammonium chloride may be used. When used, the benzalkonium halide may be benzalkonium halide in its unpurified state, which comprises a mixture of varying chain-length compounds, or it can be any suitable purified compound including those having a chain length of from about 12 to about 18 carbon atoms, including but not limited to C12, C13, C14, C15, C16, C17, and C18 compounds. By way of example, the initiator may be a quaternary ammonium chloride salt such as benzyltrialkyl ammonium chloride (BTAC).

Other initiators or accelerators may also be selected by one of ordinary skill in the art without undue experimentation. Such suitable initiators or accelerators may include, but are not limited to, detergent compositions; surfactants; e.g., nonionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfite, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

Mixtures of two or more, such as three, four, or more, initiators or accelerators may be used. A combination of multiple initiators or accelerators may be beneficial, for example, to tailor the initiator of the polymerizable monomer species. For example, where a blend of monomers is used, a blend of initiators may provide superior results to a single initiator. For example, the blend of initiators can provide one initiator that preferentially initiates one monomer, and a second initiator that preferentially initiates the other monomer, or can provide initiation rates to help ensure that both monomer species are initiated at equivalent, or desired non-equivalent, rates. In this manner, a blend of initiators can help minimize the amount of initiator necessary. Furthermore, a blend of initiators may enhance the polymerization reaction kinetics.

In Operation

Fill Directly on Tissue

Figure 22A:
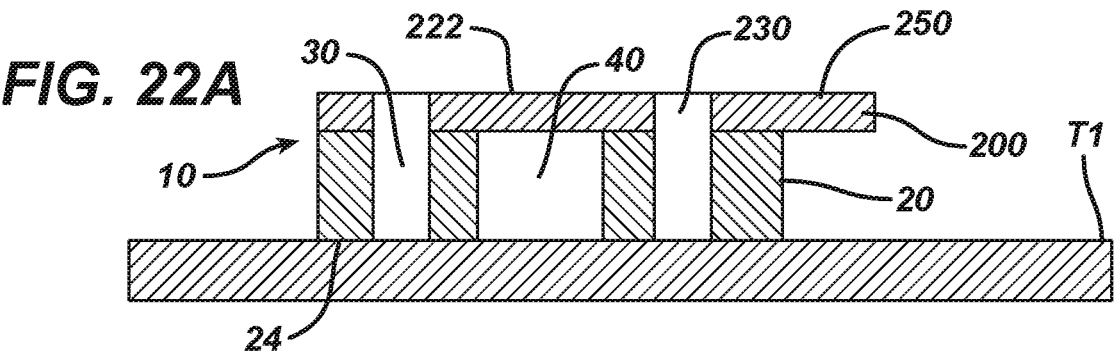
FIGS. 22A-D show embodiments of the device in operation in a schematic side cross-sectional view.

In operation, and referring now to FIG. 22, showing a schematic cross-sectional side view similar to the views shown in FIG. 14 or 16, device 10 comprising scaffold 20 with top cover 200 is positioned on tissue T1, with tissue T1 adjacent to and in contact with lower surface 24 as seen in FIG. 22A.

Optionally, prior to positioning device 10 onto tissue T1, optional bottom cover 300 is removed. Optionally, scaffold 20 is immobilized on tissue by optional pressure sensitive adhesive 50 or 52 disposed on lower surface 24.

Figure 22B:
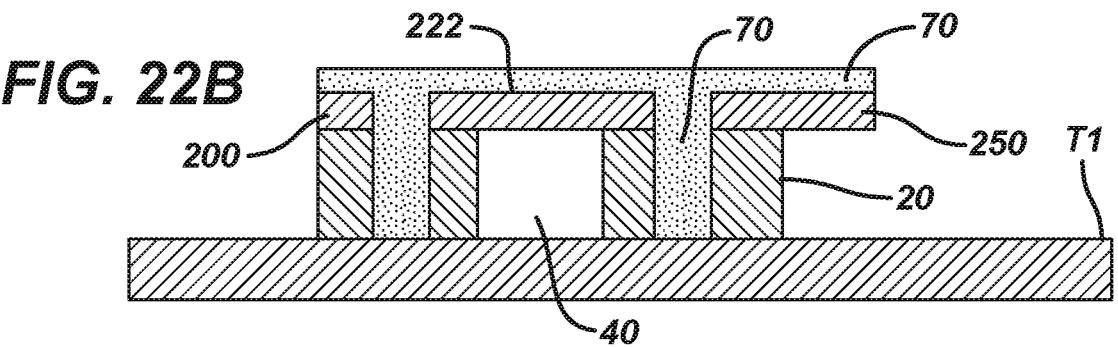

As shown in FIG. 22B, a cross-linkable or polymerizable liquid or semi-liquid adhesive 70 is then applied onto top cover 200 upper surface 222 allowing adhesive 70 to penetrate into top cover passages 230 and from there into first passages 30, filling first passages 30 as shown. Excess adhesive 70 is also shown on top cover 200 upper surface 222. Advantageously, adhesive 70 is not able to penetrate into second passages 40. Adhesive 70 starts bonding to tissue T1 at discrete zones or points defined by first passages 30.

Figure 22C:
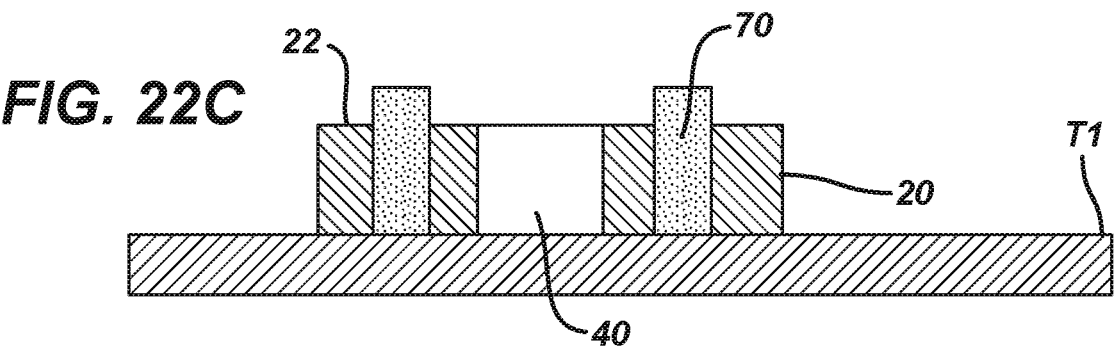

Top cover 200 is then removed, preferably by pulling on tab 250, with scaffold 20 remaining on tissue T1 as shown in FIG. 22C, with adhesive 70 filling first passages 30 and upper surface 22 exposed.

Figure 22D:
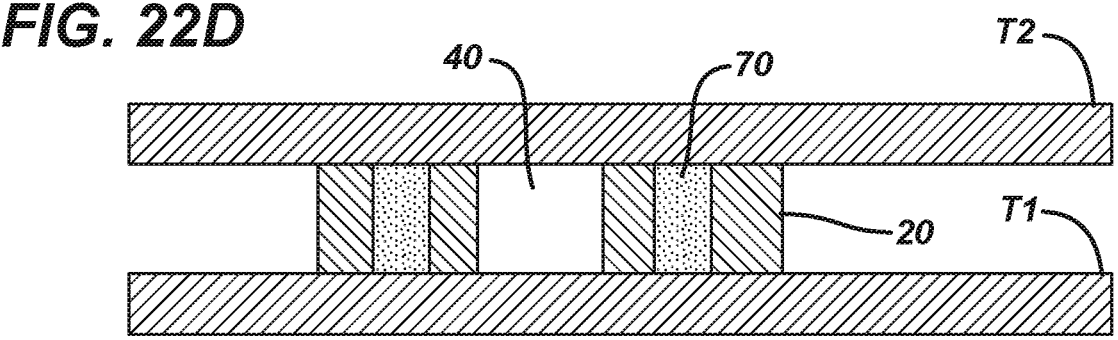

As further shown in FIG. 22D, second tissue T2 is then brought into contact with upper surface 22 thus sandwiching scaffold 20 between tissues T1 and T2 and bringing adhesive 70 contained within first passages 30 into contact also with tissue T2. Adhesive 70 establishes a bond at its interfaces with tissues T1 and T2 and is also polymerized and/or crosslinks inside first passages 30.

Thus tissues T1 and T2 which are being adhesively joined are adhesively bound to each other by adhesive 70 at discrete zones or points defined by first passages 30. At the same time, tissues T1 and T2 are exposed to each other and can establish contact through second passages 40 which are not filled with adhesive 70.

In Operation

Indirect Fill

In an alternative operation method, and referring now to FIG. 23, showing a schematic cross-sectional side view similar to the views shown in FIG. 14 or 16, device 10 comprising scaffold 20 with top cover 200 and bottom cover 300 is initially positioned with top cover 200 upper surface 222 facing upwards. As shown in FIG. 23A, cross-linkable or polymerizable adhesive 70 is then applied onto top cover 200 upper surface 222 allowing adhesive 70 to penetrate into top cover passages 230 and from there into first passages 30, filling first passages 30 as shown. Excess adhesive 70 is also shown on top cover 200 upper surface 222. Advantageously, adhesive 70 is not able to penetrate into second passages 40.

Figure 23A:
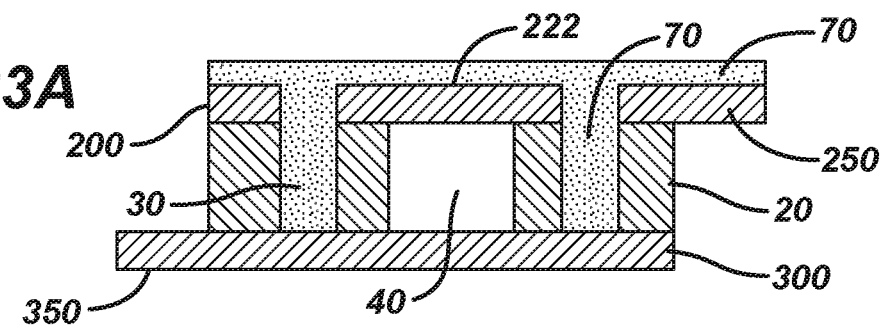
FIGS. 23A-E show embodiments of the device in operation in a schematic side cross-sectional view.
Figure 23B:
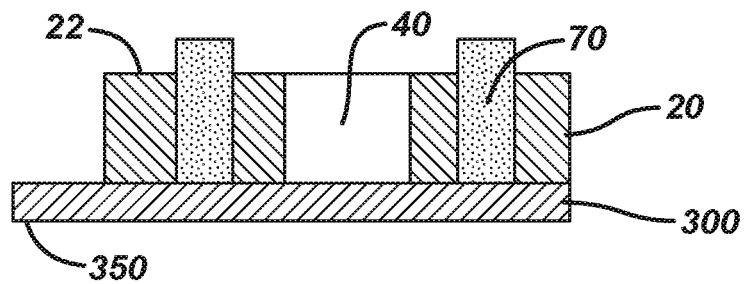

Top cover 200 is then removed, optionally by pulling on tab 250, leaving scaffold 20 with bottom cover 300 attached and with adhesive 70 filling first passages 30 and upper surface 22 exposed as shown in FIG. 23B.

Figure 23C:
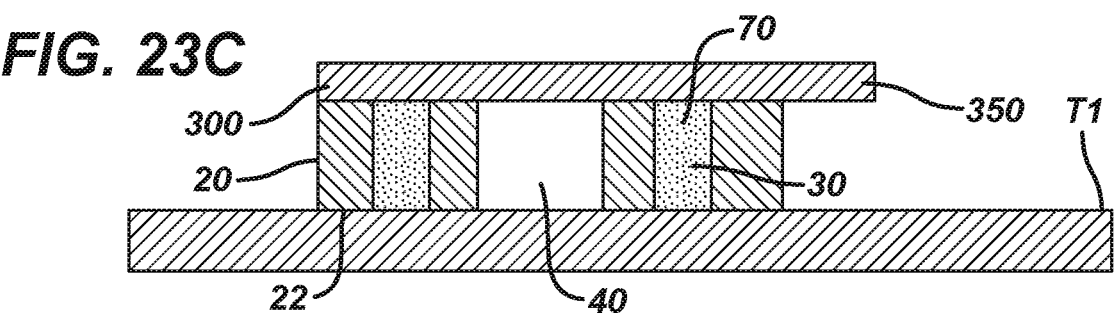

As shown in FIG. 23C, scaffold 20 with bottom cover 300 is then turned with upper surface 22 towards tissue T1 and brought into contact with tissue T1, positioning scaffold 20 on tissue T1 with tissue T1 adjacent to and in contact with upper surface 22. Adhesive 70 starts bonding to tissue T1 at discrete zones or points defined by first passages 30.

Optionally, scaffold 20 is further immobilized on tissue by optional pressure sensitive adhesive disposed on upper surface 22 (not shown).

Figure 23D:
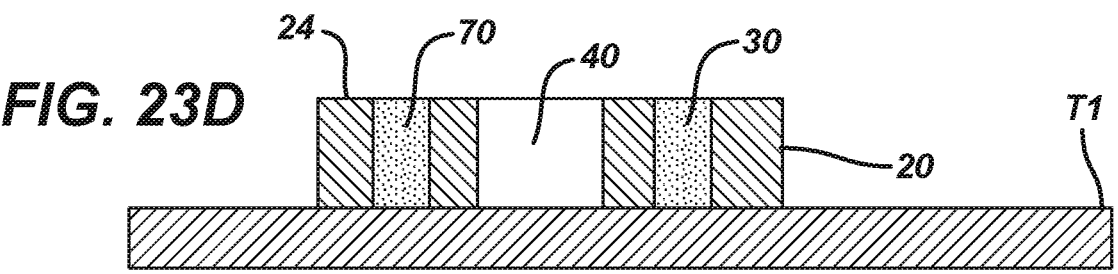

Bottom cover 300 is then removed, optionally by pulling on tab 350, leaving scaffold 20 on tissue T1 with adhesive 70 filling first passages 30 and lower surface 24 exposed as shown in FIG. 23D.

Figure 23E:
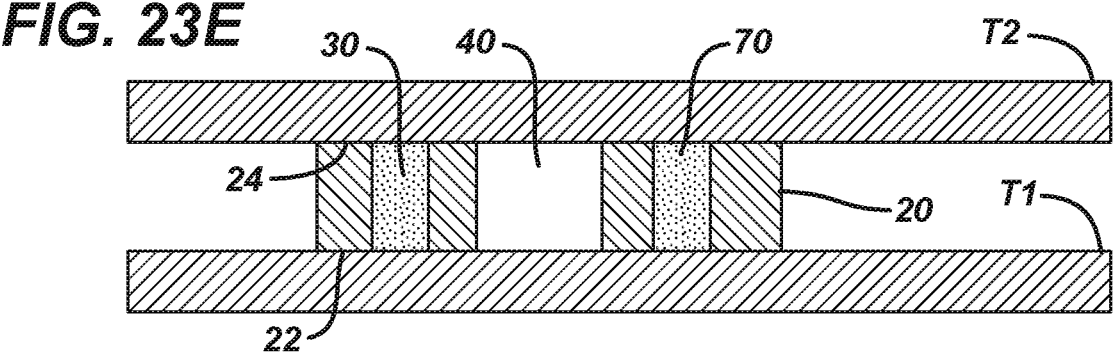

As shown in FIG. 23E, second tissue T2 is then brought into contact with lower surface 24 thus sandwiching scaffold 20 between tissues T1 and T2 and bringing adhesive 70 contained within first passages 30 into contact also with tissue T2. Adhesive 70 establishes a bond at interfaces with tissue T1 and T2 and is also polymerized and/or crosslinks inside first passages 30.

Thus tissues T1 and T2 which are being adhesively joined are adhesively bound to each other by adhesive 70 at discrete zones or points defined by first passages 30. At the same time, tissues T1 and T2 are exposed to each other and can establish contact through second passages 40 which are not filled with adhesive 70.

Advantageously, areas of tissues T1 and T2 where no bonding has occurred can contact each other and establish healing contact through second passages 40. Beneficially, scaffold 20 positioned between layers of tissue T1 and T2 enables uniform distribution of liquid adhesive for joining the layers of tissue together at discrete fixation points and not over the whole areas of exposed tissues, enabling tissue to tissue contact.

Eventually scaffold 20 resorbs or dissolves, leaving discrete adhesive connections between layers of tissue.

Adhesive

In one embodiment, liquid or semi-liquid adhesive 70 is polymerized or is cross-linking upon contact with tissues T1 and T2. In a more preferred embodiment, adhesive 70 is polymerized or is cross-linking after coming in contact with initiators and/or accelerators of adhesive polymerization and/or cross-linking.

Such initiators and/or accelerators can be coated or disposed non-releasably, i.e. immobilized in or on the scaffold 20 while retaining activity to initiate or accelerate polymerization and/or cross-linking. In one embodiment, initiators and/or accelerators are disposed releasably, i.e. they can be at least partially released into and mix with flowing adhesive 70.

In a preferred embodiment, adhesive 70 is polymerized or is cross-linking after coming in contact with initiators and/or accelerators 60 releasably disposed in first openings 30, and/or with initiators and/or accelerators 62 releasably disposed on bottom cover 300.

Rapid polymerization and/or crosslinking of adhesive 70 in contact with tissues T1 and T2 results in bonding of tissues T1 and T2 to each other through scaffold 20 at discrete points of bonding corresponding to first passages 30 and more specifically corresponding to first upper openings 32 and first lower openings 34.

Advantageously, cross-linking or polymerizing of adhesive 70 is initiated once adhesive 70 has advanced into first openings 30.

Adhesive 70 can be any type of biocompatible and rapidly cross-linkable and/or polymerizable compound or mixture of compounds. Rapidly cross-linkable and/or polymerizable means that after initiators or accelerators are added, or after the adhesive is formed from two or more components, it is capable of curing, i.e. cross-linking and/or polymerizing within 0.2 min to about 20 min, more preferably within 0.5 min to 10 min, such as 1, 2, 3, 5 min.

In one embodiment, adhesive 70 is formed prior to injection into scaffold 20, for instance by mixing two components contained in separate barrels or a two-barrel syringe, by passing these two components through a mixing tip. In this embodiment, there is no crosslinking initiator or accelerator disposed inside of scaffold 20. In one embodiment, adhesive 70 is formed by mixing fibrinogen and thrombin together.

In one embodiment, adhesive 70 comprises fibrinogen, and crosslinking initiator or accelerator disposed inside of scaffold 20 comprises thrombin.

In a preferred embodiment, the polymerizable adhesive composition may comprise a polymerizable monomeric adhesive. In embodiments, the polymerizable adhesive composition comprises a polymerizable 1,1-disubstituted ethylene monomer formulation. In embodiments, the polymerizable adhesive composition comprises a cyanoacrylate formulation. In embodiments, synthetic polymerizable adhesive materials such as polyurethane, polyethylene glycol, acrylates, glutaraldehyde and biologically based adhesives may be used.

Suitable .alpha.-cyanoacrylate monomers which may be used, alone or in combination, include alkyl .alpha.-cyanoacrylates such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate or other .alpha.-cyanoacrylate monomers such as methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers are ethyl, n-butyl, or 2-octyl .alpha.-cyanoacrylate. Other cyanoacrylate monomers which may be used include alkyl ester cyanoacrylates, such as those prepared by the Knoevenagel reaction of an alkyl cyanoacetate, or an alkyl ester cyanoacetate, with paraformaldehyde, subsequent thermal cracking of the resultant oligomer and distillation.

Many other adhesive formulations can be used and are known to a skilled artisan. For example, mixtures containing PEG succinimidyl glutarate can be used as a flowable adhesive.

It should be understood that the foregoing disclosure and description of the embodiments of the present invention are illustrative and explanatory thereof and various changes in the size, shape and materials as well as in the description of the preferred embodiment may be made without departing from the spirit of the invention.

What is claimed is:

1. A method of adhesively joining layers of tissue together using a device configured to join two layers of tissue, the device having a substantially flat and flexible scaffold having an upper surface; a lower surface and sidewalls, a plurality of first passages penetrating the scaffold from the upper surface to the lower surface; a plurality of second passages penetrating the scaffold from the upper surface to the lower surface; a substantially flat and flexible top cover releasably attached to the upper surface and covering all of the upper surface, the top cover having a plurality of top cover passages aligned with the plurality of first passages, wherein the method, comprising the steps of:
a) dispensing a fluid adhesive onto the top cover and filling the plurality of first passages with the adhesive through the plurality of top cover passages, wherein the plurality of second passages are not filled with adhesive;
b) removing the top cover from the scaffold;
c) positioning the scaffold between a first tissue and a second tissue and establishing contact of the adhesive in the plurality of first passages with the first and the second tissue;
d) polymerizing and/or cross-linking the adhesive in contact with the first and second tissue, thus bonding the first and second tissue to each other through the scaffold at discrete points of bonding;
e) establishing direct contact between the layers of tissue through the plurality of second passages; and
f) leaving the scaffold between the first and the second tissues.

2. The method of claim 1, further comprising the step of the adhesive reacting with an initiator and or accelerator disposed in or on the scaffold.

3. The method of claim 1, wherein the adhesive comprises cyanoacrylate monomers, fibrinogen, or PEG succinimidyl glutarate.

4. The method of claim 1, further comprising the steps performed prior to step a) of:
1) removing a bottom cover from the scaffold;
2) positioning the scaffold with the lower surface in contact with the first tissue; and.

5. The method of claim 1, further comprising the steps performed after step b) of:
1) contacting the upper surface of the scaffold with the first tissue; and
2) removing a bottom cover from the scaffold.

6. The method of claim 1, further comprising the steps performed prior to step a) of:
immobilizing the scaffold on the first tissue through a pressure sensitive adhesive optionally disposed on the lower surface.

7. The method of claim 1, further comprising the steps performed after step b) of:
immobilizing the scaffold on the first tissue through a pressure sensitive adhesive optionally disposed on the lower surface.

8. A method of adhesively joining layers of tissue together using a device configured to join two layers of tissue, the device having a substantially flat and flexible scaffold having an upper surface; a lower surface and sidewalls, a plurality of first passages penetrating the scaffold from the upper surface to the lower surface; a plurality of second passages penetrating the scaffold from the upper surface to the lower surface; a substantially flat and flexible top cover releasably attached to the upper surface and covering all of the upper surface, the top cover having a plurality of top cover passages aligned with the plurality of first passages; and a substantially flat and flexible bottom cover releasably attached to said lower surface and covering all of said lower surface, the bottom cover having no apertures aligned with the plurality of first passages or the plurality of second passages, wherein the method comprises the steps of:
a) removing the bottom cover from the scaffold;
b) positioning the scaffold onto a first tissue bringing the lower surface in contact with the first tissue;
c) dispensing a fluid adhesive onto the top cover and filling the plurality of first passages through the plurality of top cover passages, wherein the plurality of second passages are not filled with adhesive;
d) removing the top cover from the scaffold;
e) bringing a second tissue in contact with the upper surface, thus establishing contact of the adhesive in the plurality of first passages with the first and the second tissue;

f) polymerizing and/or cross-linking the adhesive in contact with the first and the second tissue, thus bonding the first and the second tissue to each other through the scaffold at discrete points of bonding;
g) establishing direct contact between the layers of tissue through the plurality of second passages; and
h) leaving the scaffold between the first and the second tissues.

9. The method of claim 8, further comprising the step of the adhesive reacting with an initiator and or accelerator disposed in or on the scaffold.

10. The method of claim 8, further comprising:
immobilizing the scaffold on the first tissue through a pressure sensitive adhesive optionally disposed on the lower surface.

* * * * *